United States Patent [19]

Lane et al.

[11] Patent Number: 5,593,834
[45] Date of Patent: Jan. 14, 1997

[54] METHOD OF PREPARING DNA SEQUENCES WITH KNOWN LIGAND BINDING CHARACTERISTICS

[75] Inventors: Michael J. Lane, Baldwinsville, N.Y.; Albert S. Benight, Schaumburg, Ill.; Brian D. Faldasz, Maynard, Mass.

[73] Assignee: The Research Foundation of State University of New York, Albany, N.Y.

[21] Appl. No.: 427,863

[22] Filed: Apr. 26, 1995

Related U.S. Application Data

[63] Continuation of Ser. No. 78,759, Jun. 17, 1993, abandoned.
[51] Int. Cl.$^6$ .............................. C12Q 1/68; C12Q 1/70; C12P 19/34; C07H 21/04
[52] U.S. Cl. .................. 435/6; 435/91.1; 435/91.2; 435/5; 536/24.3; 536/24.33
[58] Field of Search .................... 435/5, 6, 91.1, 435/91.2; 536/24.3, 24.31

[56] References Cited

PUBLICATIONS

Kollmann et al (1992) "Design of polymerase chain reaction primers for the selective amplification of HIV–1 RNA in the presence of HIV–1 DNA" AIDS 6:547–552.

Lowe et al (1990) "A computer program for selection of oligonucleotide primers for polymerase chain reactions" Nucl. Acids Res. 18:1757–1761.

Breslauer et al (1986) "Predicting DNA duplex stability from the base sequence" Proc. Natl. Acad. Sci 83:3746–3750.

Rychlik (1993) "Selection of primers for polymerase chain reaction" in PCR protocols, v. 15 of Methods in Mol. Biol., White, ed. Totowa, N.J.: Humana Press, pp. 31–40.

Amaratunga, M. et al., "Studies of DNA Dumbbells. II. Construction and Characterization of DNA Dumbbells with a 16 Base–Pair Duplex Stem and $T_n$ End Loops (n=2,3,4, 6,8,10,14)" *Biopolymers*, vol. 21, pp. 865–869 (1992).

Doktycz, M. et al., "Studies of DNA Dumbbells. I. Melting Curves of 17 DNA Dumbbells with Different Duplex Stem Sequences Linked by $T_4$ Endloops: Evaluation of the Nearest–Neighbor Stacking Interactions in DNA" *Biopolymers*, vol. 32, pp. 849–864 (1992).

Goldstein, R. F. and A. S. Benight, "How Many Numbers Are Required to Specify Sequence–Dependent Properties of Polynucleotides?" *Biopolymers*, vol. 32, pp. 1679–1693 (1992).

Bishop, K. D. et al., "Actinomycin D induced DNase I hypersensitivity and asymmetric structure transmission in a DNA dodecamer" *Nucleic Acids Research*, vol. 19, pp. 871–875 (1991).

McGhee, J. D. "Theoretical Calculations of the Helix–Coil Transition of DNA in the Presence of Large, Cooperatively Binding Ligands" *Biopolymers*, vol. 15, pp. 1345–1375 (1976).

*Primary Examiner*—George C. Elliott
*Assistant Examiner*—Scott D. Priebe
*Attorney, Agent, or Firm*—Lahive & Cockfield

[57] ABSTRACT

A method for determining at least one DNA sequence that can be employed as a flanking sequence to a DNA binding site for a ligand, wherein the DNA binding site is located within a preselected DNA sequence, to provide a relative increase, decrease, or approximate equality in binding constant of the ligand for its DNA binding site, or relative composite reaction rate for the ligand and a DNA sequence. Also provided are applications of the method to determine DNA primers useful in conjunction with DNA amplification to detect the presence or absence of DNA sequences and to diagnose diseases related to viral DNA, such as human immunodeficiency virus.

11 Claims, 7 Drawing Sheets

| MOLECULE | | ABBREVIATION |
|---|---|---|
| AAAAAGCTTTTT<br>TTTTTCGAAAAA (SEQ ID NO:5) | | $(AA)_2$ |
| ATATAGCTATAT<br>TATATCGATATA (SEQ ID NO:4) | | $(AT)_2$ |
| AAAAAAGCTTTTTTT<br>TTTTTTTCGAAAAAAA (SEQ ID NO:3) | | $(AA)_3$ |
| ATATATAGCTATATAT<br>TATATATCGATATATA (SEQ ID NO:2) | | $(AT)_3$ |
| AAATATAGCTATATTT<br>TTTATATCGATATAAA (SEQ ID NO:6) | | $(AA)(AT)_2$ |
| AAAAAAAAGCTTTTTTTTT<br>TTTTTTTTCGAAAAAAAA (SEQ ID NO:8) | | $(AA)_4$ |
| ATATATATAGCTATATATAT<br>TATATATATCGATATATATA (SEQ ID NO:7) | | $(AT)_4$ |

*FIG. 1*

METHOD OF PREPARING DNA SEQUENCES WITH KNOWN LIGAND BINDING CHARACTERISTICS

This invention was made with government support under grant #GM-39471 from the National Institutes of Health. Accordingly, the U.S. Government retains certain rights in the invention.

This application is a Continuation of application Ser. No. 08/078,759 filed on Jun. 17, 1993, now abandoned

BACKGROUND OF THE INVENTION

This invention relates to the field of DNA sequence design and construction comprising a method for determining DNA sequences with selected reaction attributes, such as binding affinities for their respective ligands, and for preparing such DNA sequences for various uses including as primers for diagnostic and analytical procedures to detect the presence of viral DNA.

Reactions between duplex DNA and ligands are largely dictated and mediated by the interplay of structural, thermodynamic and dynamic characteristics of DNA, and recognition mechanisms of reacting ligands. Ligands that bind to DNA span a broad range of sizes from small cations to large proteins and assembled protein aggregates. A wide variety of experimental strategies have been employed to examine sequence specificity exhibited by ligands that interact with DNA. Sequence dependent variations in local conformation and charge configuration along DNA are thought to be the principle means by which ligands discriminate between various DNA sequences. Such discrimination can be divulged and quantitatively evaluated from sequence specific thermodynamic binding parameters evaluated in studies of ligand/DNA complex formation.

Double helical DNA structure is maintained by a number of forces. Among these are the strong Coulombic interactions between phosphates along and across the backbone, hydrogen bonding between base pairs (bps) across the helix axis, stacking interactions between bps along one strand and across the helix axis and a multiplicity of interactions with charged solvent components. Inadequate understanding of these interactions precludes the construction of a realistic atomic model that correctly simulates the helixcoil or melting transition in DNA.

The most successful analytical approaches to modeling the helix-coil transition in DNA relate to the statistical thermodynamic formalism of the modified Ising model (R. M. Wartell and A. S. Benight, *Physics Rpts.*, 126, 67–107 (1985)). In this approach the central assumption is that each bp of a DNA helix can occupy only one of two possible states. These are the "intact" and "broken" states. In the intact state a given bp is presumed to be hydrogen bonded and completely stacked with its neighboring bps on either side. Alternatively, in the broken or melted state a bp is not hydrogen bonded and is completely unstacked from its neighbors on either side.

In most models, melting stability arises from independent contributions of individual bps. More sophisticated models consider nearest-neighbor (n—n) interactions. Comparison of actual absorbance-versus-temperature measurements (melting curves) with calculations allow evaluation of the sequence-dependent energetics of DNA melting within the context of the two-state per bp model.

Over the past 30 years optical and calorimetric melting studies of duplex DNA have established that the melting temperature, $t_m$, of DNA is a linearly increasing function of the percent of the bps that are of the guanine-cytosine type (%G.C). Greater stability of DNA with increased %G.C can be most readily attributed to the fact that G.C bps, with three hydrogen bonds are more stable than A.T bps with only two hydrogen bonds. Sequence dependent stacking interactions between neighboring bps may also contribute to this difference in a minor way. Thus to first order, DNA stability can be expressed as a number-weighted sum of the individual energies of two components, these being the "energies" of A.T and G.C bps. For a specific sequence, i, this energy (the H-bond energy) can be designated:

$$\Delta G_{H\,bond}(i) = \Delta S_{AT} N_{AT} T_{AT} + \Delta S_{GC} N_{GC} T_{GC} \quad (1)$$

$N_{AT}$ and $N_{GC}$ are the numbers of A.T and G.C bps in the sequence and $T_{AT}$ and $T_{GC}$ are the average melting temperatures of A.T (T.A) and G.C (C.G) bps. Values of $T_{AT}$ or $T_{GC}$ evaluated from melting curve analysis of a variety of DNAs collected as a function of solvent environment provide the dependence of $t_m$ on solvent ionic strength. The dependence of $T_{AT}$ and $T_{GC}$ on $[Na^+]$[22] was first reported by M.D. Frank-Kamenetski (Biopolymers, 10, 2623–24 (1971)).

$$T_{AT} = 355.55 + 7.95 \ln [Na^+] \quad (2a)$$

$$T_{GC} = 391.55 + 4.89 \ln [Na^+] \quad (2b)$$

$\Delta S_{AT}$ and $\Delta S_{GC}$ in eqn (1) are the average entropy changes associated with melting A.T or G.C bps. Calorimetric and spectrophotometric melting studies of long DNA polymers of natural and synthetic origins have revealed the transition entropies of melting A.T and G.C bps are virtually independent of bp type (A.T or G.C), temperature, and only weakly dependent on solvent ionic strength over reasonable limits (15 mM to 1.0M NaCl). Assuming only three preferred conformations are available for each nucleotide residue per bp, the transition entropy in forming a helix can be written as:

$$\Delta S = -2(6R \cdot \ln 3) = -26.2 \text{ cal/K.mol} \quad (3)$$

Coincidentally, this value is almost precisely the entropy of base pair formation, $\Delta S = -24.85 \pm 1.84$ cal/K.mole, determined from the studies mentioned above. Thus, $\Delta S_{AT} = \Delta S_{GC} = \Delta S$ can be determined from the ratio:

$$\Delta H_{AT}/T_{AT} = \Delta H_{GC} T_{GC} = \Delta S \quad (4)$$

where $\Delta H_{AT}$ and $\Delta H_{GC}$ are enthalpy changes in melting A.T or G.C bps. Calorimetric and spectrophotometric melting studies of short duplex oligomers six to eight bps in length have revealed a sequence dependence of the melting entropy (K. J. Breslauer, et al., *Proc. Nat. Acad. Sci. USA*, 83, 3746–50 (1986)).

The values of the bp transition enthalpies, $\Delta H_{AT}$ and $\Delta H_{GC}$, are also dependent on solvent ionic strength. Empirically derived equations for their determination in different $Na^+$ environments have also been reported. S. A. Kozyaukin, et al., *J. Biomol. Struct. Dynam.*, 5, 119–26 (1987).

$$\Delta H_{AT} = -9300 - 456.01 \ln [Na^+] \quad (5)$$

From eqns (2b) and (4), $\Delta H_{GC}$ can be determined. Therefore, if DNA is considered to be comprised of only two energetic components, the free-energy can be determined from the sequence by substitution of the appropriate values from eqns. 2, 4 and 5 in eqn. 1.

During the mid-70's substantial quantities of homogeneously pure DNA samples were available. In addition, spectrophotometric instrumentation allowed automated collection of melting curve data with increased resolution. These developments made possible the discovery of multi-model melting or "fine-structure" on optical melting transitions of heterogeneous-sequence DNA fragments. Such fine structure was attributed to sequential melting of large DNA domains. Failure of simple two-component melting theories to accurately predict the observed fine structure in DNA melting curves suggested a role for both sequence heterogeneity and sequence type in the transition.

The potential for bound ligands to affect the structure of unbound flanking DNA sequences has been recognized for some time (reviewed by D. M. Crothers and M. Fried, Cold. Spring *Harbor Symposia Quant. Biol.*, 47, 263–69 (1983)). Foot-printing methodology has been applied to detect unbound, but structurally perturbed regions flanking a ligand binding site. The location of actinomycin D binding was monitored by the inaccessibility of DNaseI to. DNA within the drug binding site. M. Lane, et al., *Proc. Nat. Acad. Sci USA*, 80, 3260–64 (1983); C. M. L. Low, et al., *Nucl. Acids Res.*, 12, 4865–79 (1984). Structural perturbations imparted to flanking DNA sequences by the bound drug were simultaneously monitored as enhanced DNaseI cleavage rates at immediately flanking sequence positions not sterically occluded from DNaseI by bound drug. Although the potential of DNA structural distortions at regions within the drug footprint exist, the footprinting approach cannot detect such distortions since these regions are protected from cleavage. When intercalated at its dinucleotide site in a linear molecule, actinomycin D can affect flanking DNA structure in a linear DNA molecule over considerable distances albeit with sequence dependence. Further corroboration that drug induced DNaseI detected enhancements were structural in origin was independently obtained from proton NMR experiments of d[(AAATATAGCTATATTT)$_2$] SEQ. ID NO: 1) complexed with actinomycin D. K. D. Bishop et al., *Nucl. Acids Res.*, 19, 871–75 (1991).

Restriction enzymes cleave duplex DNA at specific nucleotide sequences. The sequences flanking a restriction enzyme recognition site can influence the rate of restriction enzyme cleavage at the site. M. C. Aloyo, et al., *Biophys. J.*, 64, A280 (1993). Such effects occur while cleaving P4 phage DNA with the restriction enzyme EcoRI, suggesting that differences in DNA sequences flanking EcoRI sites account for observed differences in rates of cleavage. Goldstein, et al., *Virology*, 66, 420–427 (1975). A large body of data regarding the sequence-dependent behavior of various restriction enzymes has appeared. Armstrong and Bauer, *Nucl. Acids Res.*, 11, 4109–4126 (1983), and Alves, et al., *Eur. J. Biochem.*, 140, 83–92 (1984), disclosed cleavage rate variations for the enzymes EcoRI, HinfI, and PstI, finding that the activities of all three enzymes could be inhibited by long runs of GC-rich sequences placed immediately flanking the restriction sites. Concerning effects of flanking DNA sequence on cleavage by enzymes FnuDII, HaeIII, HhaI and MspI, Drew and Travers, *Nucl. Acids Res.*, 13, 4445–4456 (1985), observed that cleavage rates for these enzymes exhibit a dependence on flanking sequence; noting that the effect "though clearly evident, was complex and varied."

Variations in rates of restriction enzyme cleavage have also been shown to be dependent on DNA substrate length. Thus, the rate of cleavage at a specific site depends directly on the length of DNA flanking the specific site. Richter and Eigen, *Biophys. Chem.*, 2, 255–263 (1974); Berg, et al., *Biochemistry*, 20, 6929–6948 (1981).

The present invention offers the potential to develop highly accurate protocols using DNA amplification strategies (such as those based on the polymerase chain reaction) for the diagnosis of disease states caused by viral DNA and difficult to determine with high certainty by any known method in the art, in part because of significant analytical difficulties in reliably detecting the identity of the related DNA sequences at ultralow levels. An important example of a DNA disease virus is human immunodeficiency virus, wherein false positives can have serious psychological and social consequences.

BRIEF DESCRIPTION OF THE DRAWING

A more complete understanding of the invention and many of its advantages will become apparent by reference to the detailed description which follows when considered in conjunction with the accompanying drawing, wherein:

FIG. 1. Seven DNA molecules prepared according to the invention.

SUMMARY OF THE INVENTION

Figure 2:
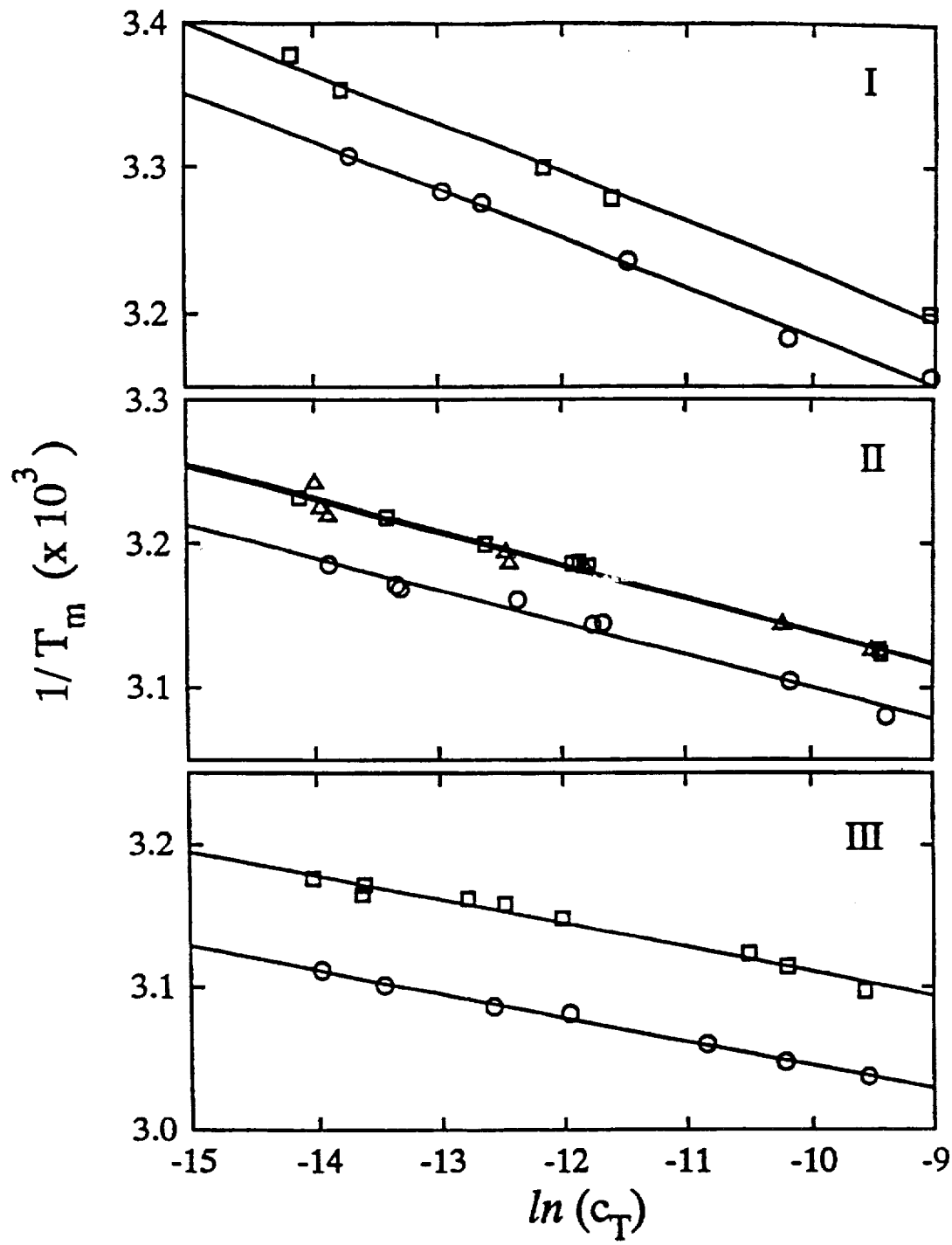
FIG. 2. Van't Hoff plots ($1/T_m$ vs. ln $c_T$) for the DNA molecules in FIG. 1. Plots for the 12-mers are shown in panel I. Plots for the 16-mers are shown in panel II. Plots for the 20-mers are shown in Panel III. Symbols: squares, $(AT)_n$; circles, $(AA)_n$; triangles, $AA(AT)_2$.

One object of the present invention is to provide a method for determining at least one DNA sequence that can be employed as a flanking sequence to a DNA binding site for a ligand, wherein the DNA binding site is located within a preselected or native DNA sequence, to provide an increase in relative binding constant of the ligand for its DNA binding site, or an increase in relative composite rate of reaction of the ligand with the DNA binding site, relative to that for a preselected or native reference flanking sequence, which comprises iterating through the preselected or native DNA sequence to provide DNA subsequences; selecting the DNA subsequences or permuting the nucleotide bases in the DNA subsequences to provide potential DNA flanking sequences; calculating free energies $\Delta G_D{}^o$ of duplex melting for each potential flanking sequence, which comprises summing free-energy values for hydrogen-bonding and stacking interactions for the nucleotide bases constituting each potential flanking sequence, wherein such free-energy values are predetermined by semi-empirical thermochemical methods; determining calculated relative composite reaction rates for the selected potential DNA flanking sequences by means of the equation:

$$\ln(k''/k') = (\kappa/RT)(\Delta G_D^{o\prime} - \Delta G_D^{o\prime\prime}),$$

or, if the relative composite relative reaction rates are binding limited, the calculated relative binding constants by means of the equation:

$$\ln(K''/K') = (\kappa/RT)(\Delta G_D^{o\prime} - \Delta G_D^{o\prime\prime}),$$

wherein $k'$ and $k''$ are relative composite rate constants of a reaction for any two DNA sequences I and II, respectively, $K'$ and $K''$ are relative binding constants for the ligand to any two DNA sequences I and II, respectively, R is the universal gas constant, T is absolute temperature, $\kappa$ is a proportionality constant or function, wherein $\kappa$ is predetermined in accord with said equations for the ligand and for set sequence length by calculating free energies of melting $\Delta G_D^o$ for at least two preselected DNA flanking sequences if $\kappa$ is a proportionality constant, or at least three if a function, determined in accord with the summing step; measuring relative or actual composite rates of reaction or binding constants for synthetic or native DNA sequences containing the preselected DNA flanking sequences; and relating the measured relative composite rates of reaction or binding constants to their respective differences in free energy of melting $\Delta G_D^o$ as determined in accord with said equations; and choosing at least one potential DNA flanking sequence to serve as a DNA flanking sequence to a DNA binding site for a ligand providing an increase in relative binding constant of the ligand for its DNA binding site, or an increase in relative composite rate of reaction of the ligand with the DNA binding site, relative to that for a preselected or native reference flanking sequence.

Another object of the present invention is to provide a method for determining at least one DNA sequence that can be employed as a flanking sequence to a DNA binding site for a ligand, wherein the DNA binding site is located within a preselected or native DNA sequence, to provide a decrease in relative binding constant of the ligand for its DNA binding site, or a decrease in relative composite rate of reaction of the ligand with the DNA binding site, relative to that for a preselected or native reference flanking sequence, which comprises iterating through the preselected or native DNA sequence to provide DNA subsequences; selecting the DNA subsequences or permuting the nucleotide bases in the DNA subsequences to provide potential DNA flanking sequences; calculating free energies $\Delta G_D^o$ of duplex melting for each potential flanking sequence, which comprises summing free-energy values for hydrogen-bonding and stacking interactions for the nucleotide bases constituting each potential flanking sequence, wherein such free-energy values are predetermined by semi-empirical thermochemical methods; determining calculated relative composite reaction rates for the selected potential DNA flanking sequences by means of the equation:

$$\ln(k''/k') = (\kappa/RT)(\Delta G_D^{o\prime} - \Delta G_D^{o\prime\prime}),$$

or, if the relative composite relative reaction rates are binding limited, the calculated relative binding constants by means of the equation:

$$\ln(K''/K') = (\kappa/RT)(\Delta G_D^{o\prime} - \Delta G_D^{o\prime\prime}),$$

wherein $k'$ and $k''$ are relative composite rate constants of a reaction for any two DNA sequences I and II, respectively, $K'$ and $K''$ are relative binding constants for the ligand to any two DNA sequences I and II, respectively, R is the universal gas constant, T is absolute temperature, $\kappa$ is a proportionality constant or function, wherein $\kappa$ is predetermined in accord with said equations for the ligand and for set sequence length by calculating free energies of melting $\Delta G_D^o$ for at least two preselected DNA flanking sequences if $\kappa$ is a proportionality constant, or at least three if a function, determined in accord with the summing step; measuring relative or actual composite rates of reaction or binding constants containing the preselected DNA flanking sequences; and relating the measured relative composite rates of reaction or binding constants to their respective differences in free energy of melting $\Delta G_D^o$ as determined in accord with said equations; and choosing at least one potential DNA flanking sequence to serve as a DNA flanking sequence to a DNA binding site for a ligand providing a decrease in relative binding constant of the ligand for its DNA binding site, or a decrease in relative composite rate of reaction of the ligand with the DNA binding site, relative to that for a preselected or native reference flanking sequence.

A further object of the present invention is to provide a method for determining at least one DNA sequence that can be employed as a flanking sequence to a DNA binding site for a ligand, wherein the DNA binding site is located within a preselected or native DNA sequence, to provide an approximately equal relative binding constant of the ligand for its DNA binding site, or an approximately equal relative composite rate of reaction of the ligand with the DNA binding site, relative to that for a preselected or native reference flanking sequence, which comprises iterating through the preselected or native DNA sequence to select DNA subsequences; selecting the DNA subsequences or permuting the nucleotide bases in the DNA subsequences to provide potential DNA flanking sequences; calculating free energies $\Delta G_D^o$ of duplex melting for each potential DNA flanking sequence, which comprises summing free-energy values for hydrogen-bonding and stacking interactions for the nucleotide bases constituting each potential DNA flanking sequence, wherein such free-energy values are predetermined by semi-empirical thermochemical methods; determining calculated relative composite reaction rates for the potential DNA flanking sequences by means of the equation:

$$\ln(k''/k') = (\kappa/RT)(\Delta G_D^{o\prime} - \Delta G_D^{o\prime\prime}),$$

or, if the relative composite relative reaction rates are binding limited, the calculated relative binding constants by means of the equation:

$$\ln(K''/K') = (\kappa/RT)(\Delta G_D^{o\prime} - \Delta G_D^{o\prime\prime}),$$

wherein $k'$ and $k''$ are relative composite rate constants of a reaction for any two DNA sequences I and II, respectively, $K'$ and $K''$ are relative binding constants for the ligand to any two DNA sequences I and II, respectively, R is the universal gas constant, T is absolute temperature, $\kappa$ is a proportionality constant or function, wherein $\kappa$ is predetermined in accord with said equations for the ligand and for set sequence length by calculating free energies of melting $\Delta G_D^o$ for at least two preselected DNA flanking sequences if $\kappa$ is a proportionality constant, or at least three if a function, determined in accord with the summing step; measuring relative or actual composite rates of reaction or binding constants for synthetic or native DNA sequences containing the preselected DNA flanking sequences; and relating the measured relative composite rates of reaction or binding constants to their respective differences in free energy of melting $\Delta G_D^o$ as determined in accord with said equations; and choosing at least one potential DNA flanking sequence to serve as a DNA flanking sequence to a DNA binding site for a ligand providing an approximately equal relative binding constant of the ligand for its DNA binding site, or an approximately equal in relative composite rate of reaction of the ligand with the DNA binding site, relative to that for a preselected or native reference flanking sequence.

DETAILED DESCRIPTION OF THE INVENTION

The present invention utilizes (a) thermochemical data to evaluate duplex stability of DNA sequences flanking a binding site or a site of reaction and either (b) relative binding constants for binding DNA sequences containing the flanking sequences or (c) relative composite rates of reaction involving such DNA sequences and a ligand. A direct correlation derived therefrom between duplex stability and either relative binding constant or composite reaction rate provides a rule for determining at least one DNA sequence that can be employed as a flanking sequence to a DNA binding site for the ligand with resulting relative increase, decrease, or equality in binding constant of the ligand for its binding site or in composite reaction rate for reaction between the ligand and the DNA sequence. The present invention therefore provides a method which allows adjustment of reaction or binding parameters of a DNA sequence towards a ligand, including but not limited to a restriction enzyme, ligase, or polymerase. Critical to the success of the method is the accuracy of the energetic parameters needed to perform thermochemical calculations of relative energies of DNA sequences. A correspondence between the calculated energies and measured binding ligand constants or composite rates of reaction for a particular ligand allows the prediction of the direction of adjustment in binding or reaction rate for DNA sequences containing other flanking sequences.

The present invention makes possible the design and preparation of reagents comprising DNA sequences with modified flanking regions with predictable DNA binding/reactivity characteristics.

The present invention therefore provides a method for determining at least one DNA sequence that can be employed as a flanking sequence to a DNA binding site for a ligand, wherein the DNA binding site is located within a preselected or native DNA sequence, to provide an increase in relative binding constant of the ligand for its DNA binding site, or an increase in relative composite rate of reaction of the ligand with the DNA binding site, relative to that for a preselected or native reference flanking sequence, which comprises iterating through the preselected or native DNA sequence to provide DNA subsequences; selecting the DNA subsequences or permuting the nucleotide bases in the DNA subsequences to provide potential DNA flanking sequences; calculating free energies $\Delta G_D^o$ of duplex melting for each potential flanking sequence, which comprises summing free-energy values for hydrogen-bonding and stacking interactions for the nucleotide bases constituting each potential flanking sequence, wherein such free-energy values are predetermined by semi-empirical thermochemical methods; determining calculated relative composite reaction rates for the selected potential DNA flanking sequences by means of the equation:

$$\ln (k^{II}/k^{I}) = (\kappa/RT)(\Delta G_D^{oI} - \Delta G_D^{oII}),$$

or, if the relative composite relative reaction rates are binding limited, the calculated relative binding constants by means of the equation:

$$\ln (K^{II}/K^{I}) = (\kappa/RT)(\Delta G_D^{oI} - \Delta G_D^{oII}),$$

wherein $k^{I}$ and $k^{II}$ are relative composite rate constants of a reaction for any two DNA sequences I and II, respectively, $K^{I}$ and $K^{II}$ are relative binding constants for the ligand to any two DNA sequences I and II, respectively, R is the universal gas constant, T is absolute temperature, $\kappa$ is a proportionality constant or function, wherein $\kappa$ is predetermined in accord with said equations for the ligand and for set sequence length by calculating free energies of melting $\Delta G_D^o$ for at least two preselected DNA flanking sequences if $\kappa$ is a proportionality constant, or at least three if a function, determined in accord with the summing step; measuring relative or actual composite rates of reaction or binding constants-for synthetic or native DNA sequences containing the preselected DNA flanking sequences; and relating the measured relative composite rates of reaction or binding constants to their respective differences in free energy of melting $\Delta G_D^o$ as determined in accord with said equations; and choosing at least one potential DNA flanking sequence to serve as a DNA flanking sequence to a DNA binding site for a ligand providing an increase in relative binding constant of the ligand for its DNA binding site, or an increase in relative composite rate of reaction of the ligand with the DNA binding site, relative to that for a preselected or native reference flanking sequence.

The present invention also provides a method for determining at least one DNA sequence, that can be employed as a flanking sequence to a DNA binding site for a ligand., wherein the DNA binding site is located within a preselected or native DNA sequence, to provide a decrease in relative binding constant of the ligand for its DNA binding site, or a decrease in relative composite rate of reaction of the ligand with the DNA binding site, relative to that for a preselected or native reference flanking sequence, which comprises iterating through the preselected or native DNA sequence to provide DNA subsequences; selecting the DNA subsequences or permuting the nucleotide bases in the DNA subsequences to provide potential DNA flanking sequences; calculating free energies $\Delta G_D^o$ of duplex melting for each potential flanking sequence, which comprises summing free-energy values for hydrogen-bonding and stacking interactions for the nucleotide bases constituting each potential flanking sequence, wherein such free-energy values are predetermined by semi-empirical thermochemical methods; determining calculated relative composite reaction rates for the selected potential DNA flanking sequences by means of the equation:

$$\ln (k^{II}/k^{I})=(\kappa/RT)(\Delta G_D^{oI}-\Delta G_D^{oII}),$$

or, if the relative composite relative reaction rates are binding limited, the calculated relative binding constants by means of the equation:

$$\ln (K^{II}/K^{I})=(\kappa/RT)(\Delta G_D^{oI}-\Delta G_D^{oII}),$$

wherein $k^I$ and $k^{II}$ are relative composite rate constants of a reaction for any two DNA sequences I and II, respectively, $K^I$ and $K^{II}$ are relative binding constants for the ligand to any two DNA sequences I and II, respectively, R is the universal gas constant, T is absolute temperature, κ is a proportionality constant or function, wherein κ is predetermined in accord with said equations for the ligand and for set sequence length by calculating free energies of melting $\Delta G_D^o$ for at least two preselected DNA flanking sequences if $\kappa$ is a proportionality constant, or at least three if a function, determined in accord with the summing step; measuring relative or actual composite rates of reaction or binding constants for synthetic or native DNA sequences containing the preselected DNA flanking sequences; and relating the measured relative composite rates of reaction or binding constants to their respective differences in free energy of melting $\Delta G_D^o$ as determined in accord with said equations; and choosing at least one potential DNA flanking sequence to serve as a DNA flanking sequence to a DNA binding site for a ligand providing a decrease in relative binding constant of the ligand for its DNA binding site, or a decrease in relative composite rate of reaction of the ligand with the DNA binding site, relative to that for a preselected or native reference flanking sequence.

The present invention further provides a method for determining at least one DNA sequence that can be employed as a flanking sequence to a DNA binding site for a ligand, wherein the DNA binding site is located within a preselected or native DNA sequence, to provide an approximately equal relative binding constant of the ligand for its DNA binding site, or an approximately equal relative composite rate of reaction of the ligand with the DNA binding site, relative to that for a preselected or native reference flanking sequence, which comprises iterating through the preselected or native DNA sequence to select DNA subsequences; selecting the DNA subsequences or permuting the nucleotide bases in the DNA subsequences to provide potential DNA flanking sequences; calculating free energies $\Delta G_D^o$ of duplex melting for each potential DNA flanking sequence, which comprises summing free-energy values for hydrogen-bonding and stacking interactions for the nucleotide bases constituting each potential DNA flanking sequence, wherein such free-energy values are predetermined by semi-empirical thermochemical methods; determining calculated relative composite reaction rates for the potential DNA flanking sequences by means of the equation:

$$\ln (K''/K') = (\kappa/RT)(\Delta G_D^{oI} - \Delta G_D^{oII}),$$

or, if the relative composite relative reaction rates are binding limited, the calculated relative binding constants by means of the equation:

$$\ln (K''/K') = (\kappa/RT)(\Delta G_D^{oI} - \Delta G_D^{oII}),$$

wherein $k'$ and $k''$ are relative composite rate constants of a reaction for any two DNA sequences I and II, respectively, $K'$ and $K''$ are relative binding constants for the ligand to any two DNA sequences I and III respectively, R is the universal gas constant, T is absolute temperature, $\kappa$ is a proportionality constant or function, wherein $\kappa$ is predetermined in accord with said equations for the ligand and for set sequence length by calculating free energies of melting $\Delta G_D^o$ for at least two preselected DNA flanking sequences if $\kappa$ is a proportionality constant, or at least three if a function, determined in accord with the summing step; measuring relative or actual composite rates of reaction or binding constants for synthetic or native DNA sequences containing the preselected DNA flanking sequences; and relating the measured relative composite rates of reaction or binding constants to their respective differences in free energy of melting $\Delta G_D^o$ as determined in accord with said equations; and choosing at least one potential DNA flanking sequence to serve as a DNA flanking sequence to a DNA binding site for a ligand providing an approximately equal relative binding constant of the ligand for its DNA binding site, or an approximately equal in relative composite rate of reaction of the ligand with the DNA binding site, relative to that for a preselected or native reference flanking sequence.

In one embodiment, the invention provides a method for determining at least one set of DNA primers which amplify or generate amplification products for at least two different regions from a corresponding preselected or native DNA sequence at approximately equal rates, which comprises iterating through the preselected or native DNA sequence to select at least one DNA subsequence for use as a potential DNA primer or set of DNA primers; calculating free energies $\Delta G_D^o$ of duplex melting for each potential DNA primer, by summing free-energy values for hydrogen-bonding and stacking interactions for the nucleotide bases constituting each potential DNA primer, wherein such free-energy values are predetermined by semi-empirical thermochemical methods; determining calculated relative composite reaction rates for amplifying the corresponding preselected or native DNA sequence using each selected or permuted potential DNA primer or set of DNA primers by means of the equation:

$$\ln (K''/K') = (\kappa/RT)(\Delta G_D^{oI} - \Delta G_D^{oII}),$$

or, if the relative composite reaction rates are binding limited, determining calculated relative binding constants of the corresponding preselected DNA sequence by means of the equation:

$$\ln (K''/K') = (\kappa/RT)(\Delta G_D^{oI} - \Delta G_D^{oII}),$$

wherein $k'$ and $k''$ are relative composite reaction rate constants for amplification using potential DNA primers I and II, respectively, $K'$ and $K''$ are relative binding constants for an amplifying reagent binding to the preselected or native DNA sequence to which potential DNA primers I and II anneal, respectively, R is the universal gas constant, T is absolute temperature, $\kappa$ is a proportionality constant or function, wherein $\kappa$ is predetermined in accord with said equations for the amplifying reagent and for set sequence length by relating measured relative composite rates of amplification or binding with potential DNA primers or set of potential DNA primers I and II to their respective differences in free energies of melting $\Delta G_D^{oI}$ and $\Delta G_D^{oII}$, which comprises calculating free energies of melting $\Delta G_D^o$ for at least two potential DNA primers if $\kappa$ is a proportionality constant, or at least three if a function, determined in accord with the summing step; measuring relative or actual composite rates of amplification or generation of amplification products or relative binding constants for synthetic or native DNA sequences to which the potential DNA primers anneal; and relating the measured relative composite rates of reaction or relative binding constants to their respective differences in free energy of melting $\Delta G_D^o$ in accord with said equations; and synthesizing the potential DNA primers by chemical or biochemical methods; measuring relative or actual composite reaction rates of amplification or generation of amplification products using the potential DNA primers by any method suited for the purpose, comprising gel techniques, spectroscopic methods, electrochemical methods, and biochemical assay methods; repeating the iterating, calculating, synthesizing and measuring steps to determine at least one additional potential DNA primer which amplifies the preselected or native DNA sequence, does not interact with any other primer, and has a relative composite reaction rate approximately equal to that of the first potential DNA primer or set of potential DNA primers; and choosing at least one set of potential DNA primers with approximately equal calculated relative composite reaction rates for amplifying or generating amplification products for at least two different regions from the corresponding preselected or native DNA sequence using each set of potential DNA primers, wherein calculated relative composite reaction rates fall within a predefined deviation about a mean relative composite reaction rate.

In another embodiment, the invention provides a method of detecting the presence or absence of a preselected or native DNA sequence or sequences which comprises determining at least one set of DNA primers which amplify, or generate amplification products for, at least two different regions from the preselected or native DNA sequence at approximately equal rates, by iterating through the preselected or native DNA sequence to select at least one DNA subsequence for use as a potential DNA primer or set of DNA primers; calculating free energies $\Delta G_D^o$ of duplex melting for each potential DNA primer, which comprises summing free-energy values for hydrogen-bonding and stacking interactions for the nucleotide bases constituting each potential DNA primer, wherein such free-energy values are predetermined by semi-empirical thermochemical methods; determining calculated relative composite reaction rates for amplifying the corresponding preselected or native DNA sequence using each selected or permuted potential DNA primer or set of DNA primers by means of the equation:

$$\ln (K^{II}/K^{I}) = (\kappa/RT)(\Delta G_D^{oI} - \Delta G_D^{oII}),$$

or, if the relative composite reaction rates are binding limited, determining calculated relative binding constants of the corresponding preselected DNA sequence by means of the equation:

$$\ln (K^{II}/K^{I}) = (\kappa/RT)(\Delta G_D^{oI} - \Delta G_D^{oII}),$$

wherein k$^I$ and k$^{II}$ are relative composite reaction rate constants for amplification using potential DNA primers I and II, respectively, K$^I$ and K$^{II}$ are relative binding constants for an amplifying reagent binding to the preselected or native DNA sequence to which potential DNA primers I and II anneal, respectively, R is the universal gas constant, T is absolute temperature, κ is a proportionality constant or function, wherein κ is predetermined in accord with said equations for the amplifying reagent and for set sequence length by relating measured relative composite rates of amplification or binding with potential DNA primers or set of potential DNA primers I and II to their respective differences in free energies of melting $\Delta G_D^{oI}$ and $\Delta G_D^{oII}$ which comprises calculating free energies of melting $\Delta G_D^o$ for at least two potential DNA primers if κ is a proportionality constant, or at least three if a function, determined in accord with the summing step; measuring relative or actual composite rates of amplification or generation of amplification products or relative binding constants for synthetic or native DNA sequences to which the potential DNA primers anneal; and relating the measured relative composite rates of reaction or relative binding constants to their respective differences in free energy of melting $\Delta G_D^o$ in accord with said equations; and synthesizing the potential DNA primers by chemical or biochemical methods; measuring relative or actual composite reaction rates of amplification or generation of amplification products using the potential DNA primers by any method suited for the purpose, comprising gel techniques, spectroscopic methods, electrochemical methods, and biochemical assay methods; repeating the iterating, calculating, synthesizing and, measuring steps to determine at least one additional potential DNA primer which amplifies, or generates amplification products for, the preselected or native DNA sequence, does not interact with any other primer, and has a relative composite reaction rate approximately equal to that of the first potential DNA primer or set of potential DNA primers; and choosing at least one set of potential DNA primers with approximately equal calculated relative composite reaction rates for amplifying, or generating amplification products for, at least two different regions from the corresponding preselected or native DNA sequence using each set of potential DNA primers, wherein calculated relative composite reaction rates fall within a predefined deviation about a mean relative composite reaction rate; and using at least one set of potential DNA primers to detect the presence or absence of a preselected or native DNA sequence, which comprises combining aliquots of at least one set of DNA primers with an analytical unknown sample which may or may not contain a preselected or native DNA sequence; performing the amplifying reaction to generate amplified concentrations or amplification products of the preselected or native DNA sequence, if present; and observing by any suitable qualitative or quantitative method the presence or absence of, the preselected or native DNA sequence, wherein suitable methods include gel techniques, spectroscopic methods, electrochemical methods, or-biochemical assay methods, thereby detecting the presence or absence of the preselected or native DNA sequence.

In another embodiment, the invention provides a method of detecting the presence or absence of a preselected or native DNA sequence or sequences, which if present in a subject indicates that the subject is suffering from a disease or diseases related to the respective preselected or native DNA sequence or sequences, which comprises determining at least one set of DNA primers which amplify, or generate amplification products for, at least two different regions from the corresponding DNA sequence at approximately equal rates, by iterating through the preselected or native DNA sequence or sequences to select at least one DNA subsequence for use as a potential DNA primer or set of DNA primers; calculating free energies $\Delta G_D^o$ of duplex melting for each potential DNA primer, which comprises: summing free-energy values for hydrogen-bonding and stacking interactions for the nucleotide bases constituting each potential DNA primer, wherein such free-energy values are predetermined by semi-empirical thermochemical methods; determining calculated relative composite reaction rates for amplifying, or generating amplification products for, the corresponding preselected or native DNA sequence or sequences using each potential selected or permuted DNA primer or set of DNA primers by means of the equation:

$$\ln (K^{II}/K^{I}) = (\kappa/RT)(\Delta G_D^{oI} - \Delta G_D^{oII}),$$

or, if the relative composite reaction rates are binding limited, determining calculated relative binding constants of the corresponding preselected or native DNA sequences by means of the equation:

$$\ln (K^{II}/K^{I}) = (\kappa/RT)(\Delta G_D^{oI} - \Delta G_D^{oII}),$$

wherein k$^I$ and k$^{II}$ are relative composite reaction rate constants for amplification using potential DNA primers I and II, respectively, K$^I$ and K$^{II}$ are relative binding constants for an amplifying reagent binding to the preselected or native DNA sequence to which potential DNA primers I and II anneal, respectively, R is the universal gas constant, T is absolute temperature, κ is a proportionality constant or function, wherein κ is predetermined in accord with said equations for the amplifying reagent and for set sequence length by relating measured relative composite rates of amplification or binding with potential DNA primers or set of potential DNA primers I and II to their respective differences in free energies of melting $\Delta G_D^{o\prime}$ and $\Delta G_D^{o\prime\prime}$, which comprises: calculating free energies of melting $\Delta G_D^o$ for at least two potential DNA primers if κ is a proportionality constant, or it least three if a function, determined in accord with the summing step; measuring relative or actual composite rates of amplification or generation of amplification products or relative binding constants for synthetic or native DNA sequences to which the potential DNA primers anneal; and relating the measured relative composite rates of reaction or relative binding constants to their respective differences in free energy of melting $\Delta G_D^o$ in accord with said equations; and synthesizing the potential DNA primers by chemical or biochemical methods; measuring relative or actual composite reaction rates of amplification or generation of amplification products using the potential DNA primers by any method suited for the purpose, comprising gel techniques, spectroscopic methods, electrochemical methods, and biochemical assay methods; repeating the iterating, calculating, synthesizing and measuring steps to determine at least one additional potential DNA primer which amplifies, or generates amplification products for, the preselected or native DNA sequence, does not interact with any other primer, and has a relative composite reaction rate approximately equal to that of the first potential DNA primer or set of potential DNA primers; and choosing at least one set of potential DNA primers with approximately equal calculated relative composite reaction rates for amplifying, or generating amplification products for, at least two different regions from the corresponding preselected or native DNA sequence using each set of potential DNA primers, wherein the calculated relative composite reaction rates fall within a predefined deviation about a mean relative composite reaction rate; and using at least one set of potential DNA primers for two different regions of the preselected or native DNA sequence or sequences to detect the presence or absence of a preselected or native DNA sequence or sequences, which if present indicates that a subject is suffering from a disease or diseases related to the respective preselected or native DNA sequence or sequences, which comprises combining aliquots of at least one set of DNA primers with an analytical unknown sample which may or may not contain a preselected or native DNA sequence or sequences; performing the amplification reaction to generate amplified concentrations or amplification products of the preselected or native DNA sequence or sequences, if present; and observing by any suitable qualitative or quantitative method the presence or absence of, the preselected or native DNA sequence or sequences, wherein suitable methods include gel techniques, spectroscopic methods, electrochemical methods, or biochemical assay methods, thereby detecting the presence or absence of the preselected or native DNA sequence or sequences, which if present indicates that a subject is suffering from a disease or diseases related to the respective preselected or native DNA sequence or sequences.

In still another embodiment, the invention provides a method of detecting the presence or absence of a DNA sequence or sequences corresponding to human immunodeficiency virus, which comprises determining at least one set of DNA primers which amplify, or generate amplification products for, at least two different regions from the corresponding DNA sequence at approximately equal rates, by iterating through the DNA sequence or sequences corresponding to human immunodeficiency virus to select at least one DNA subsequence for use as a potential DNA primer or set of DNA primers; calculating free energies $\Delta G_D^o$ of duplex melting for each potential DNA primer, which comprises summing free-energy values for hydrogen-bonding and stacking interactions for the nucleotide bases constituting each potential DNA primer, wherein such free-energy values are predetermined by semi-empirical thermochemical methods; determining calculated relative composite reaction rates for amplifying, or generating amplification products for, the corresponding DNA sequence or sequences using each selected or permuted potential DNA primer or set of DNA primers by means of the equation:

$$\ln (k''/k') = (\kappa/RT)(\Delta G_D^{o\prime} - \Delta G_D^{o\prime\prime}),$$

or, if the relative composite reaction rates are binding limited, determining calculated relative binding constants of the corresponding preselected or native DNA sequences by means of the equation:

$$\ln (K''/K') = (\kappa/RT)(\Delta G_D^{o\prime} - \Delta G_D^{o\prime\prime}),$$

wherein k' and k'' are relative composite reaction rate constants for amplification using potential DNA primers I and II, respectively, K' and K'' are relative binding constants for an amplifying reagent binding to the DNA sequence to which potential DNA primers I and II anneal, respectively, R is the universal gas constant, T is absolute temperature, κ is a proportionality constant or function, wherein κ is predetermined in accord with said equations for the amplifying reagent and for set sequence length by relating measured relative composite rates of amplification or binding with potential DNA primers or set of potential DNA primers I and II to their respective differences in free energies of melting $\Delta G_D^{o\prime}$ and $\Delta G_D^{o\prime\prime}$, which comprises calculating free energies of melting $\Delta G_D^o$ for at least two potential DNA primers if κ is a proportionality constant, or at least three if a function, determined in accord with the summing step; measuring relative or actual composite rates of amplification or generation of amplification products or relative binding constants for synthetic or native DNA sequences to which the potential DNA primers anneal; and relating the measured relative composite rates of reaction or relative binding constants to their respective differences in free energy of melting $\Delta G_D^o$ in accord with said equations; and synthesizing the potential DNA primers by chemical or biochemical methods; measuring relative or actual composite reaction rates of amplification or generation of amplification products using the potential DNA primers by any method suited for the purpose, comprising gel techniques, spectroscopic methods, electrochemical methods, and biochemical assay methods; repeating the iterating, calculating, synthesizing and measuring steps to determine at least one additional potential DNA primer which amplifies, or generates amplification products for, the DNA sequence, does not interact with any other primer, and has a relative composite reaction rate approximately equal to that of the first potential DNA primer or set of potential DNA primers; and choosing at least one set of potential DNA primers with approximately equal calculated relative composite reaction rates for amplifying, or generating amplification products for, at least two different regions from the corresponding DNA sequence using each set of potential DNA primers, wherein the calculated relative composite reaction rates fall within a predefined deviation about a mean relative composite reaction rate; and using at least one set of potential DNA primers for two different regions of the DNA sequence or sequences to detect the presence or absence of the DNA sequence or sequences corresponding to human immunodeficiency virus, which comprises combining aliquots of at least two potential DNA primers with an analytical sample which may or may not contain the DNA sequence or sequences; performing the amplification reaction to generate amplified concentrations or amplification products of the DNA sequence or sequences, if present; and observing by any suitable qualitative or quantitative method the presence or absence of, the DNA sequence or sequences corresponding to human immunodeficiency virus, wherein suitable methods include gel techniques, spectroscopic methods, electrochemical methods, or biochemical assay methods, thereby detecting the presence or absence of the DNA sequence or sequences corresponding to human immunodeficiency virus.

As practiced in the invention, the length of the DNA subsequence selected in the iterating steps or the potential DNA flanking sequences provided in the permuting step varies from 4 to 1000 nucleotide base pairs. Preferably, these sequences vary from 4 to 75 base pairs in length.

As practiced in the invention, the term "preselected" DNA sequence may refer to a sequence of either synthetic or commercial origin. "Native" DNA sequences may refer to any DNA sequence from a natural source, including but not limited to bacterial, viral, or mammalian. Examples of DNA sequences which may be used in the practice of the invention include pBR322 plasmid, SV40 plasmid, any sequence from lambda phage, and any cloned DNA.

As practiced in the invention, the term "ligand" refers to any small molecule, any metalloorganic compound, any heterocyclic compound, or any protein which binds DNA. A ligand may be a sequence specific cleavage enzyme, such as a restriction endonuclease, including EcoRI, HaeIII, and BglI. A ligand may also refer to non-specific cleavage reagents, such as DNaseI or micrococcal nuclease. A ligand may also be DNA polymerase or DNA-dependent RNA polymerase, a helicase, a topoisomerase, or any protein which regulates the transcription or replication of DNA. In addition, ligands may refer to proteins which are associated with the structural organization of DNA in the cell nucleus, or the packaging of DNA, including histones and nucleosomes. Other ligands contemplated in the invention include DNA-binding antitumor antibiotics.

TABLE 1

NEAREST-NEIGHBOR FREE-ENERGIES

| 5'MN3' STACK | $-\Delta G_{MN}$, 25° C. (cal/mol) C (0.115 M Na$^+$) |
|---|---|
| AT | 1092 |
| TA | 966 |
| AA (TT) | 1195 |
| AC (GT) | 1764 |
| CA (TG) | 1509 |
| TC (GA) | 1802 |
| CT (AG) | 1280 |
| CG | 1887 |
| GC | 2674 |
| GG (CC) | 1908 |

TABLE 2

CALCULATED PARTIAL FREE-ENERGIES

| MOLECULE | $-\Delta G_P = -[\Sigma \Delta G_{MN} + \Delta G_{sym}]$ 25° C. (kcal/mol) |
|---|---|
| (AA)$_2$ | 14.4 |
| (AT)$_2$ | 13.1 |
| (AA)$_3$ | 19.2 |
| (AT)$_3$ | 17.2 |
| (AA)(AT)$_2$ | 17.9 |
| (AA)$_4$ | 24.0 |
| (AT)$_4$ | 21.3 |

TABLE 3

EXPERIMNTAL THERMODYNAMIC PARAMETERS

| Molecule | $-\Delta G_E$, 25° C. (kcal/mol) | $-\Delta H$ (kcal/mol) | $-\Delta S$ (cal/deg-mol) |
|---|---|---|---|
| (AA)$_2$ | 8.9 | 59.2 | 168.8 |
| (AT)$_2$ | 8.1 | 57.9 | 167.1 |
| (AA)$_3$ | 12.6 | 88.5 | 254.5 |
| (AT)$_3$ | 10.9 | 86.0 | 251.9 |
| (AA)(AT)$_2$ | 11.5 | 87.4 | 254.5 |
| (AA)$_4$ | 17.1 | 121.7 | 351.0 |
| (AT)$_4$ | 14.6 | 118.7 | 349.3 |

TABLE 4

DUPLEX INITIATION FREE-ENERGIES

| MOLECULE | $-\Delta G_{int} = \Delta G_E - \Delta G_P$, (kcal/mol)] |
|---|---|
| (AA)$_2$ | 7.1 |
| (AT)$_2$ | 6.6 |
| average: | 6.9 ± 0.3 |
| (AA)$_3$ | 8.2 |
| (AT)$_3$ | 7.9 |
| (AA)(AT)$_2$ | 8.0 |
| average: | 8.0 ± 0.1 |
| (AA)$_4$ | 8.5 |
| (AA)$_4$ | 8.3 |
| average: | 8.4 ± 0.1 |

TABLE 5

RATE CONSTANTS FOR ALU I CLEVAGE OF $(AA)_N$ AND $(AT)_N$ DUPLEXES AND $AA(AT)_2AGCT(AT)_2TT$ CHIMERIC DUPLEX

| Oligonucleotide | Length (bp) | $K_{comp}$ (min$^{-1}$, × 10$^3$) | r |
|---|---|---|---|
| $(AT)_2AGCT(AT)_2$ (SEQ ID NO: 4) | 12 | 19.0 | 0.98 |
| $(AA)_2AGCT(TT)_2$ (SEQ ID NO: 5) | 12 | 6.3 | 0.95 |
| $(AT)_3AGCT(AT)_3$ (SEQ ID NO: 2) | 16 | 11.5 | 0.98 |
| $(AA)_3AGCT(TT)_3$ (SEQ ID NO: 3) | 16 | 3.9 | 0.97 |
| $(AA)(AT)_2AGCT(AT)_2TT$ (SEQ ID NO: 6) | 16 | 7.7 | .99 |
| $(AT)_4AGCT(AT)_4$ (SEQ ID NO: 7) | 20 | 9.3 | 0.99 |
| $(AA)_4AGCT(TT)_4$ (SEQ ID NO: 8) | 20 | 3.1 | 0.95 |

TABLE 6

SUMMARY OF DIFFERENTIAL REACTIVITIES OF $(AT)_3$ AND $(AA)_3$ WITH FOUR LIGANDS

| Ligand | Physical Quantity | Value |
|---|---|---|
| Alu I | $k_{comp}((AT)_3)/k_{comp}((AA)_3)$ | ≅3 |
| Gilvocarin V[a] | $k_{adduct}((AT)_3)/k_{adduct}((AA)_3)$ | ~2.5 |
| DNAse I[b] | $k_{comp}((AT)_3)/k_{comp}((AA)_3)$ | ≥2 |
| Actinomycin D[b] | $k_{eq}((AT)_3)/k_{eq}((AA)_3)$ | ≥2 |

[a]The present work
[b]Knobler, et al. Nucl. Acids Res., 20, 4553–57 (1992)
[c]Huang, et al. Nucl. Acids Res., 16, 11125–11139 (1988)
$K_{comp}$ = composite rate constant for cleavage
$K_{adduct}$ = rate constant for UV induced adduct formation at [Gilvocarcin]/[DNA(bp)] = 1
$K_{eq}$ = estimated equilibrium binding constant from published data The following Experimental Details are set forth to aid in an understanding of the invention, and are not intended, and should not be construed, to limit in any way the invention set forth in the claims which follow thereafter.

Experimental Details.

Oligodeoxynucleotide Synthesis and Manipulations:

Oligodeoxynucleotides were synthesized on a BioSearch (Model 8600) DNA synthesizer in 1.0 μMole quantities. DNAs were purified by electrophoresis through a 20%, 7μurea polyacrylamide gel, visualized by back shadowing against a fluorecent TLC plate and the gel slice containing the purified ologomer excised from the gel with a razor blade. The gel slice was ground up and suspended in 1.0 ml of a (10 mM Tris/1.0 mM Na₂ED7A pH 7.5) solution and incubated overnight at 4° C. Subsequently, oligonuceotides were separated from the gel by passage of the slurry through silanized glass Wool and then precipitated from a 0.3M sodium acetate/70% ethanol solution. Labeling and purification of the labeled oligonucleotides has been described. M. J. Lane, et al., Nucl. Acids Res., 15, 839–52 (1987). Labeled samples were heated to 90° C. and slow cooled (1° C./min) to avoid snap-back of the molecules to themselves.

AluI Digestion:

The cleavage reaction was carried out in 10 mMTris-HCL/8 mM MgCl₂/2 mM, CaCl₂, pH 7.5. The concentration of the oligonucleotide, AluI endonuclease, and the reaction temperature (25° C.) were held constant; the time of incubation was varied. A typical reaction was performed in 6 μl:2 μl cold carrier d(ATATAGCTATAT) (SEQ. ID NO: 4) duplex, 2 μl labeled duplex and 2 μl AluI (8/1). The reaction was started by addition of the AluI and stopped by addition of 10 μl of a solution composed of 10M urea/100 mM NaoH/50 mM Na2 EDTA/0.1% bromopheral blue/0.1% xylene cyanol. Samples were then heated at 90° C. for 2 minutes, quick chilled on ice, and counted using liquid scintillation prior to loading onto a 15% denaturing polyacrylamide gel.

Autoradiography/Counting/Statistics:

Radioactive bands on the gel were localized by autoradiography. The gel slices were ground up and suspended in double distilled H₂O, and quantified by liquid scintillation counting. To determine the cleavage kinetics, the counts pertaining to full length oligonucleotide were compared to initial counts loaded at various digestion times. This date was subsequently analyzed by linear regression.

Thermochemical Methods

Evaluation of sequence-dependent energetics of nearest-neighbor stacking in DNA has been the subject of a number of melting studies using a variety of DNA samples.

If nearest-neighbor (n—n) sequence dependent interactions are the sole contribution to DNA stability, there are 16 possible different n—n stacks. However, because of the anti-parallel structure of duplex DNA, six of these possible stacks are degenerate. Thus, only 10 of the 16 possible stacks are unique and distinguishable. These unique stacks designated 5'-MN-3' are: AA=TT, AT, TA, CA=TG, GT=AC, CT=AG, GA=TC, CG, GG=CC, GC. In principle, there are 10 unique energies associated with the 10 possible unique n—n bp combinations that can be evaluated. For the evaluation of n—n sequence dependent energetics in DNA, two formats have been presented. These methods differ primarily in the formal description of the possible n—n interactions. Subsequently these formalisms are referred to as the "n—n doublet" and "single bp" formats. M. J. Doktycz, et al., Biopolymers, 32, 849–64 (1992). Distinguishing characteristics of these approaches include the different DNA samples and methods of evaluating n—n interactions from analysis of their optical melting curves.

Most experimental studies aimed at evaluating sequence-dependent stability of DNA have analyzed melting curves in terms of bp doublets, wherein n—n sequence dependence is considered to arise from the cumulative contributions of the hydrogen bonds and n—n stacking interactions associated with a two bp doublet. K. J. Breslauer, et al., Proc. Nat. Acad, Sci, USA, 83, 3746–50 (1986); S. G. Delcourt and R. D. Blake, J. Biol. Chem., 266, 15160–69 (1991); A. V. Vologodskii, et al., J. Biomol. Struct. Dynam., 2, 131–48 (1984); O. Gotoh and Y. Tagashira, Biopolymers, 20, 1033–42 1981. The individual contributions of bp hydrogen bonding and stacking are not separately distinguished.

In the individual bp stability format, contributions to DNA thermodynamic stability are apportioned into two parts, i.e. H-bonding and n—n stacking. In this way a unique n—n sequence-dependent energy can be assigned to each individual bp along the DNA. The primary component of this energy includes the average effects of ionic strength on H-bonding, phosphate-phosphate interactions at the individual bp level and the type of hydrogen bonding strength (A.T versus G.C bps) essentially as given by eqn 1. In addition to the hydrogen bonding free-energy between complementary bps on opposite strands, sequence dependent stacking interactions with neighboring bps on either side are also considered.

Therefore, the free-energy change in forming bp i depends on the type of bp i (A.T or G.C) and establishing stacking interactions with neighboring bps i-1 and i+1. $\Delta G_i$ is given by:

$$\Delta G_i = \Delta S(T_i - T) \quad (6)$$

where:

$$T_i = T_{H-B} + (\delta G_{i-1,i} + \delta G_{i,i+1})/2\Delta S \quad (7)$$

$T_{H-B} = T_{AT}$ or $T_{GC}$ is the average melting temperature of either an A.T (T.A) or G.C (C.G) type bp, this includes effects of the hydrogen bonding strength of eqn 1 and the average stacking interactions of all 10 types of n—n stacks. As written, the $\delta G_{i,i\pm1}$ terms in eqn (7) are actually deviations from the average n—n stacking free-energy specific for each type of n—n stack and can take on ten different values. The n—n interactions in this format were recently evaluated by Doktycz, et al., Id., from melting studies of a series of dumbbell molecules.

To compare n—n sequence-dependent interactions the values obtained from dumbbells must be transformed into the doublet format. As discussed by Vologodskii, et al., Id., the single bp and doublet formats can be united by defining an effective melting temperature, $T_{MN}$, of the doublet comprised of the neighboring bps M and N. Base pairs M and N each have individual melting temperatures $T_M$ and $T_N$ equal to $T_{AT}$ or $T_{GC}$ and a contribution from the stacking interactions between them. This stacking interaction is written as the deviation of $T_{MN}$ from the average melting temperatures of A.T and G.C bps due to n—n stacking, $\delta T_{MN}$, i.e.:

$$T_{MN} = (T_M + T_N)/2 + \delta T_{MN} \quad (8)$$

$$\delta T_{MN} = \delta G_{MN}/\Delta S_{MN} \quad (9)$$

Assuming $\Delta S_{MN} = \Delta S$ and substituting these expressions in equation (6), the expression for the free-energy of each n—n doublet is given by:

$$\Delta G_{MN} = \Delta S[(T_M + T_N)/2 + \delta G_{MN}/\Delta S - T] \quad (10)$$

These doublet free-energies determined from the values reported by Doktycz, et al., Id., are given in Table 1.

EXAMPLE 1

Use of n—n stacking parameters to calculate free-energies of 7 duplex DNA molecules:

The values of the 10 MN n—n stacks given in Table 1 can be appropriately summed to yield the energy of any duplex DNA sequence. The following calculations demonstrate use of Table 1.

Sequences of the seven molecules are shown in FIG. 1. The set is comprised of two 12-mers, three 16-mers and two 20-mers. Each of the DNA strands comprising the duplexes are self-complementary. When associated in the bimolecular duplexes as shown, the duplex of each molecule has the common central four bp sequence 5'-A-G-C-T-3' flanked on either side by the sequences $(AT)_n$ or $(AA)_n$, n=2,3,4 and $AA(AT)_2$. Several factors motivated the choice of the particular sequences of the molecules shown in FIG. 1. Because for each length, the number of A.T (T.A) bps is the same, only the distribution of A.T and T.A bps differs for fragments of the same length. Therefore, any differences in stability between two fragments of the same size can be attributed to differences in the n—n sequences of the fragments. Another feature of these sequences is that the central sequence is the recognition site of both the restriction enzyme AluI and the drug actinomycin D. Molecular length is such that melting temperatures conveniently fall in a range for reliable acquisition and analysis of the experimental melting curves. Finally, the sequences are short enough that their melting transitions may be accurately modeled with a two-state, all-or-none model. This facilitates a simple and straightforward van't Hoff analysis for evaluation of the thermodynamic parameters of the melting transition.

In the n—n model, the total free-energy of any given duplex DNA sequence, $\Delta G_{total}$, can be written as:

$$\Delta G_{total} = \Sigma_i \Delta G_{i,i+1} + \Delta G_{sym} + \Delta G_{int} \quad (11)$$

For an N bp sequence, the sum over i runs from 1 to N-1 and adds all the pertinent $\Delta G_{MN}$'s required for a particular sequence. $\Delta G_{sym}$ is a symmetry correction that accounts for the degeneracy in self-complementary versus non-self-complementary sequences. For duplex DNAs of the same length the entropy difference between non-self-complementary and self-complementary sequences due to symmetry is $\Delta S_{sym} = -1.4$ eu. Thus, at 298.15K, $\Delta G_{sym} = +0.41$ kcal/mol and thus introduces a slightly destabilizing effect on self-complementary sequences compared to non-self-complementary sequences. The partial free-energies defined as:

$$\Delta G_p = \Sigma_i \Delta G_{i,i+1} + G_{sym} \quad (12)$$

and calculated from the n—n values in Table 1 are listed in Table 2 for each of the DNAs shown in FIG. 1.

Table 2 reveals the calculated higher stability of the (AA) sequences over the (AT) sequences. $AA(AT)_2$ has a calculated partial free-energy intermediate between those of the $(AA)_3$ and $(AT)_3$ sequences.

In addition to the partial free-energies of eqn 12, the total free-energy must include the free-energy of helix initiation, $\Delta G_{int}$. $\Delta G_{int}$ accounts for the added difficulty of forming the first bp initiating the duplex compared to the subsequent formation of all other bps.

$$\Delta G_T = \Delta G_p + \Delta G_{int} \quad (13)$$

The length dependence of $\Delta G_{int}$ has not been clearly established. To explicitly evaluate the value of $\Delta G_{int}$, the samples in FIG. 1 were prepared and melting curves in 115 mM Na$^+$ were collected.

The single-strand DNA oligomers that anneal to form the duplexes shown in FIG. 1, were synthesized on a 1 μMol scale and characterized for purity by polyacrylamide gel electrophoresis according to established protocols. Samples were then exhaustively dialyzed versus the melting solvent (100 mM NaCl, 10 mM sodium phosphate, 1 mM EDTA, pH=7.5). When incubated at moderate ionic strength, the potential exists for self-complementary oligomers to self-associate and form bi-molecular duplexes or fold to intramolecular hairpins. The unimolecular hairpin and bimolecular duplex can be clearly distinguished by their significantly different gel electrophoretic mobility. Gel electrophoretic analysis of every sample before and after collection of melting curves indicated the only species present was the bi-molecular duplex.

Absorbance versus temperature melting curves were collected for each of the molecules at a heating rate of 60° C.

per hour over the temperature range from 5° to 85° C. Reverse curves were also collected for all samples. A data point was collected approximately every 0.1° C. For each sample, melting curves were collected as a function of strand concentration over the 200 fold range from approximately 500 nM to 100 μM strands. Absolute absorbance readings ranged from 0.08 OD to 1.3 OD. Optically matched quartz cuvettes of 1 and 0.1 cm path length were employed for the studies. All melting curves were entirely reversible upon cooling at the same rate.

Absorbance versus temperature curves were normalized to upper and lower baselines and converted to $\theta_B$ (the fraction of duplex molecules) versus temperature curves. These $\theta_B$ versus temperature curves were then analyzed assuming the transitions occur in an "all-or-none" or two-state manner. From these curves the transition temperature, $T_m$, is determined as the temperature where $\theta_B=0.5$. Assuming the transitions are two-state, the thermodynamics of the transition can be evaluated from a van't Hoff plot of $1/T_m$ versus $\ln C_T$. The linear equation describing the resulting plot is, $$1/T_m = (R/\Delta H) \ln C_T + \Delta S/\Delta H \qquad (14)$$

Clearly, from this analysis the slope of the van't Hoff plot is $R/\Delta H$ and the intercept is $\Delta S/\Delta H$.

The van't Hoff plots obtained from melting data collected on the seven linear DNA fragments of FIG. 1 are displayed in FIG. 2. All lines shown were excellent fits to the data (correlation coefficient of $R \geq 0.98$). The thermodynamic parameters determined from these plots for each of the duplex DNAs shown in FIG. 1 are listed in Table 3. The experimentally determined total free-energy:

$$\Delta G_T(E) = \Delta H - T \Delta S \qquad (15)$$

determined from $\Delta H$ and $\Delta S$ at 298.15 for each molecule is given in column 3 of Table 3.

According to eqn 13, the free-energy of helix initiation, can be determined for each fragment as:

$$\Delta G_{ini} = \Delta G_T - \Delta G_P \qquad (16)$$

Values of $\Delta G_{ini}$ determined from the differences of the appropriate values in Tables 2 and 3 are given in Table 4. Table 4 indicates $\Delta G_{ini}$ has the opposite sign of $\Delta G_P$, revealing that, as expected, helix nucleation makes a destabilizing contribution to the total free-energy of a duplex. Examination of the values of $\Delta G_{ini}$ in Table 4, reveals that $\Delta G_{ini}$ is clearly an increasing function of duplex length. The average values of $\Delta G_{ini}(N)$ for N=12, 16, 20, were determined from the differences between $\Delta G_T(E)$ and $\Delta G_P$, for fragments of the same length, and are also given in Table 4. The free-energy of helix initiation, $\Delta G_{ini}(N)$, is related to the helix nucleation parameter, B(N) as:

$$-RT \ln \beta(N) = \Delta G_{ini}(N) \qquad (17)$$

Thus, from values in Table 4, β can be evaluated.

Figure 3:
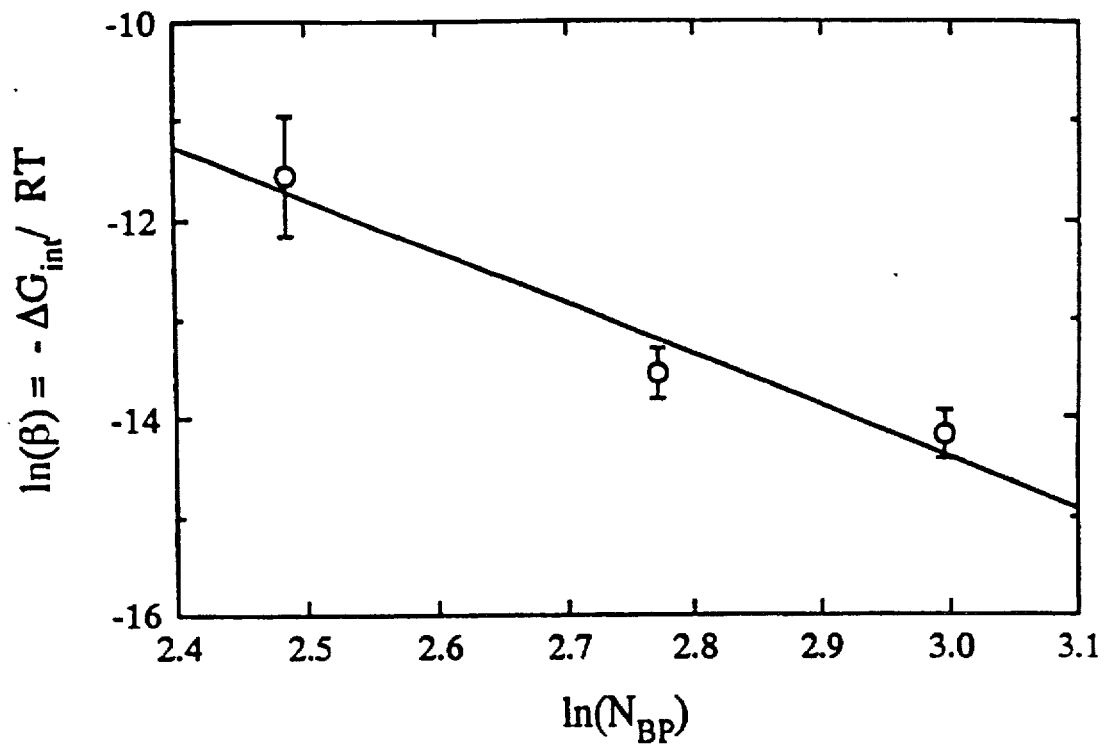
FIG. 3. Helix initiation parameter. The natural logarithm of the helix inititation parameter $\beta = -\Delta G_{ini}/RT$ is plotted vs. natural logarithm of the duplex length, $N_{bp}$. The slope of the plot is $-5.2$, indicating $\beta \sim N^{-5.2}$.
Figure 4E:
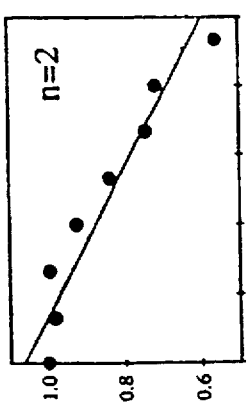
FIG. 4. Rates fc(t) of AluI cleavage of seven synthetic DNA duplexes. Fraction of full length duplex is plotted as a function of time for all seven duplexes of FIG. 1.
Figure 4F:
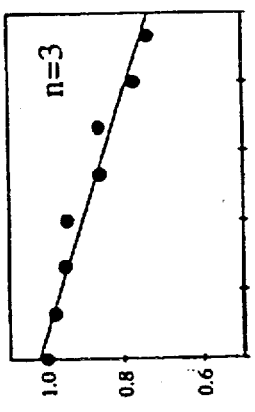
Figure 4G:
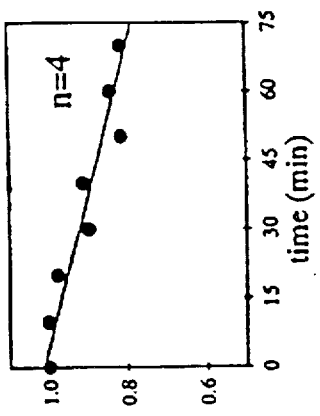
Figure 4D:
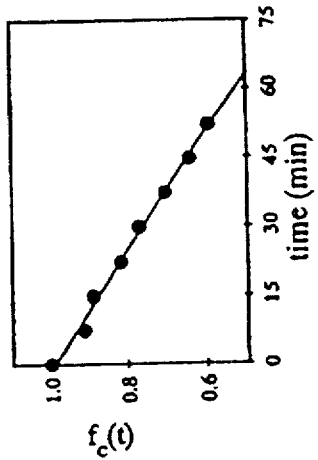
Figure 4A:
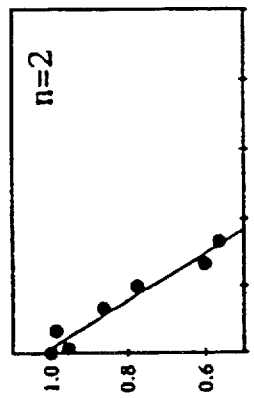
Figure 4B:
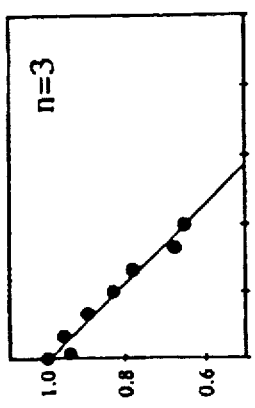
Figure 4C:
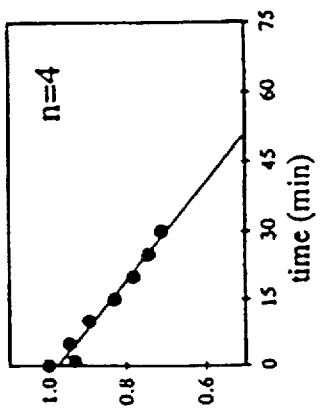

A plot of $\ln (\beta) = -\Delta G_{ini}(N)/RT$ versus $\ln (N)$ obtained from the values in Table 4 and using eqn 17 is shown in FIG. 3. The three points corresponding to fragments 12, 16 and 20 base pairs in length can be fit with a straight line as shown. From the slope and intercept of the plot the functional form of β is determined. From the resulting linear parameters we find:

$$\beta(N) = 3.4 N^{-5.2} \qquad (18)$$

Thus, β(N) is length dependent, and varies inversely with length. The value of the exponent in eqn 17 (−5.2) is in good agreement with the exponent of N (−5) obtained from a melting model where the duplex-to-single strand transition is modeled as a duplex rod melting to two single-strand rods. D. Poland and H. A. Scheraga, "Theory of Helix-Coil Transitions in Biopolymers," Academic Press, New York, pp 237–39 (1970).

EXAMPLE 2

Effect of Flanking Sequence and Length on Cleavage Rates by AluI Restriction Enzyme To examine the effects of both length and flanking sequence on restriction enzyme cleavage rate in a well-defined context, rates of cleavage of the same DNAs shown in FIG. 1 by AluI restriction enzyme were measured. These rate measurements showed that AluI restriction enzyme, which recognizes and cleaves at the central four bp sequence of these DNAs, is sensitive to the identity and length of the flanking sequence motif. To determine the relative rates of cleavage of the seven duplexes with AluI in a manner facilitating quantitative comparison of the rates produced, reactions with all duplexes were cleaved under identical enzyme and substrate concentrations. The experimental strategy for obtaining these conditions was to perform pilot experiments with all of the duplexes to establish enzyme concentrations and incubation times which could apply ubiquitously to the entire set of molecules. A fairly high concentration was used for the fastest cleaving duplex found in the set, $(AT)_2$, as a competitor for the enzyme (13 μM duplex) and a labeled duplex concentration of 10 nM (±3 nM). Labelled duplexes were pre-annealed and no hairpins were detected under annealing conditions by native polyacrylamide gels. Rate series (time course of cleavage reaction) for each duplex were repeated at least twice, and each independent rate measurement employed independently labelled duplex. The fraction of duplex remaining as full length was determined after separation of cleaved product from full length strands on 7.0M urea polyacrylamide gels followed by autoradiography and excision of full length molecules remaining with subsequent direct Cherenkov counting of gel slices. Therefore, each time point represents the average fraction remaining (relative to control experiments with no enzyme, executed in parallel) from at least two independent experiments.

Figure 5:
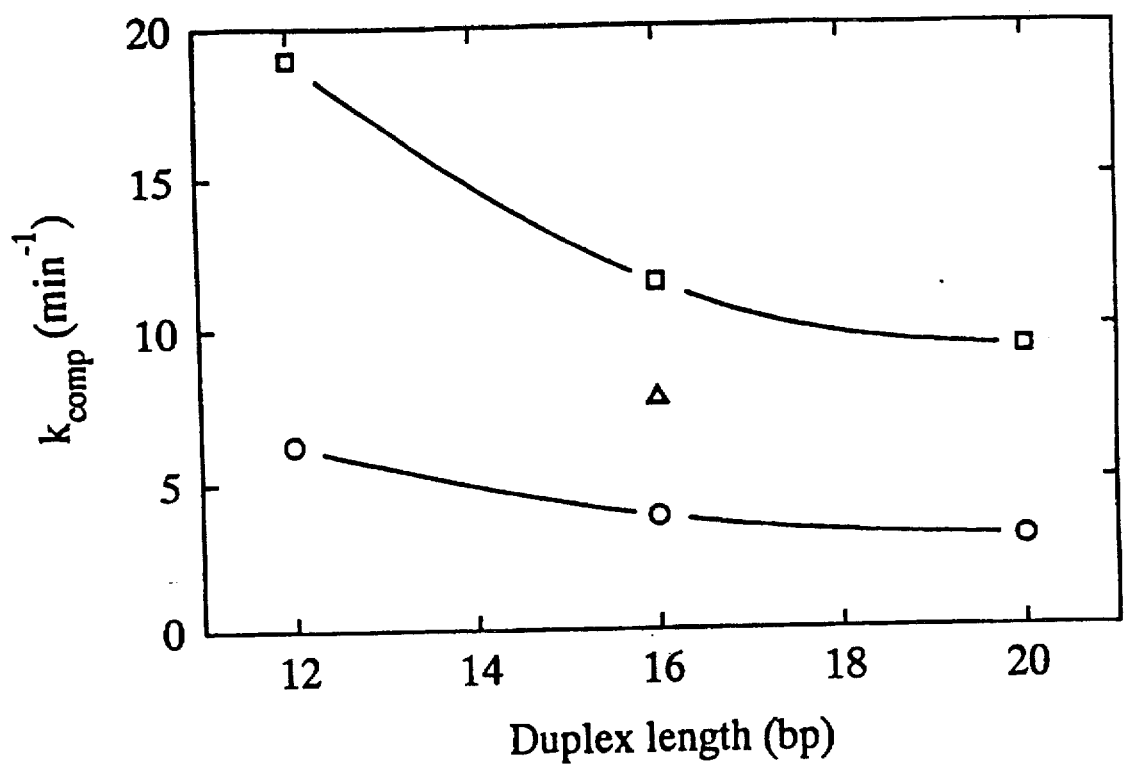
FIG. 5. Composite reaction rates vs. duplex length for the DNAs in FIG. 1. Symbols: squares, $(AT)_n$; circles, $(AA)_n$; triangles, $AA(AT)_2$.

AluI was obtained commercially (BRL). Activity was assayed by "spiking" test reactions with labelled duplex DNA halfway through a mock digestion containing carrier duplex but no label. No loss of activity was detected over the time intervals employed. At the high duplex and enzyme concentrations employed (128 units per reaction in a reaction buffer composed of 8 mM $MgCl_2$, 2 mM $CaCl_2$, 10 mM Tris-HCl, pH=7.5). Final glycerol concentration introduced with restriction enzyme was constant in all reactions at 16%. Concentration was such that the cleavage reaction kinetics would be expected to follow a first-order expression. In FIG. 4 the fraction of total uncleaved molecules versus time, $f_c(t)$, is shown for all seven duplexes. The reactions proceeded only to the point where at least 50% of the respective duplexes remained full length. This assured that the fraction of molecules remaining would be linear with respect to time, providing reliable initial velocities. A linear response of $f_c(t)$ versus time would be expected regardless of the actual kinetic order governing the digestion reaction (i.e. first- or zero-order, unsaturated or saturated enzyme, respectively). However, rate data shown in FIG. 4 verified predominantly first-order behavior in the digestions. For example, examination of the rate data for $(AT)_2$, upper left panel of FIG. 4, reveals that just over 50% of this molecule remains uncleaved after 30 minutes, while the most resistant duplex, $(AA)_4$, has more than 75% uncleaved molecules remaining after 70 minutes (lower right panel FIG. 4). Since $(AT)_2$ was present in vast, but identical, excess in all reactions, the enzyme reaction with $(AA)_4$ remained constant with time despite significant reduction in total substrate available represented by unlabelled $(AT)_2$. This condition can be met only if the enzyme was in excess in the system (e.g., the enzyme reactions follow first-order kinetics). The rate constants were determined by linear least squares fits to the $f_c(t)$ versus time data; fits for all seven duplexes were linear. Rates are shown in Table 5 along with their correlation coefficients for the linear fits. The R values in no case are lower than 0.95. In FIG. 5, the composite rate constants for cleavage, $k_{comp}$, are plotted versus duplex length. Several interesting features emerge from these plots and demonstrate the influence of duplex length and flanking sequence identity on AluI cleavage rates of these DNAs. First, cleavage rate is inversely proportional to duplex length. The rate comparison shown in FIG. 5 demonstrates that the 12-mers (in each series, i.e., $(AT)_n$ or $(AA)_n$) are cleaved at approximately 2.0 and 1.6 times faster than the 20-mer and 16-mer of the same series, respectively. Thus, increasing length (65% increase between 12 bp and 20 bp) does not result in increased enzyme cleavage of these molecules. Apparently, an enzyme diffusion mechanism (P. Berg, et al., *Biochemistry*, 20, 6929–6948 (1981)) is not rate determining. The solvent conditions of the reactions included 10 mM divalent cation which would minimize a diffusion mechanism. Second, for DNAs of the same length cleavage rates by AluI are a factor of three times higher for the $(AT)_n$ molecules than for the $(AA)_n$ molecules, i.e. $k_{comp}(AT)_2/k_{comp}(AA)_2=3.02$; $k_{comp}(AT)_3/k_{comp}(AA)_3=2.95$ and $k_{comp}(AT)_4/k_{comp}(AA)_4=3.00$. Third, the "hybrid" 16 bp molecule, $AA(AT)_2$, that contains a mixture of both AA and AT flanking sequences cleaves at a rate between those of the 16 bp molecules containing purely AT or AA flanking sequence motifs.

Comparisons of Rates of Alu I Cleavage with the Free-Energy of Duplex Melting

Figure 6:
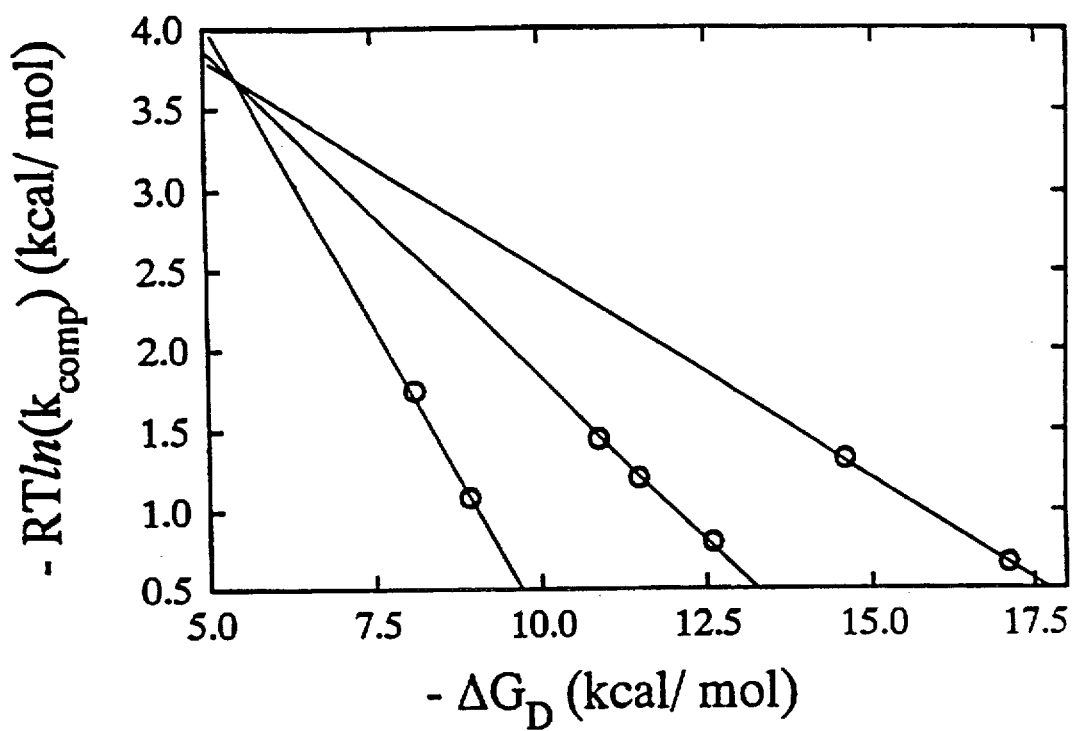
FIG. 6. Composite reaction rate vs. duplex free-energy. Note the curves pass through a common point, $\Delta G_o(O)$, $-RT$ in $R_c$ (0), which corresponds to the point where the core sequence AGCT would fall.

The cleavage rates evaluated for the seven duplexes in FIG. 1 are compared to the melting free-energies of the same molecules reported in Table 4. Plots of $-RT\ln k_{comp}$ versus $\Delta G_D$ for the seven DNAs of FIG. 1 are shown in FIG. 6. For the 12-mers and 20-mers lines were drawn through the two data points. The points for the 16-mers were fit by linear least squares. All the lines intersect at a single point. Such observations that small sequence-dependent changes in DNA equilibrium structure or stability result in relatively large increases in the rates of enzyme digestion at a specific site suggest such changes must affect the height of the activation barrier for enzyme reactivity. K. D. Bishop, et al., *Nucl. Acids Res.*, 19, 871–74 (1991). Further, the linear extrapolations in FIG. 6 suggest a linear relationship between the composite activation free-energy for enzyme cleavage and free-energy of melting the duplex. This relationship can be expressed as:

$$\Delta G^{++}=RT\ln k_{comp}=\kappa(N)\Delta G_D+\Delta G^{++}(O) \qquad (19)$$

where $\Delta G^{++}$ is the composite free-energy activation barrier for AluI cleavage of a DNA substrate of a particular length and is directly proportional to the free-energy of melting the duplex substrate. That the plots are not parallel shows that the proportionality constant, $\kappa(N)$, must be length dependent as written in eq 19. The point where all lines cross ($\Delta G_D(O)$, $-RT\ln k_c(O)$) should correspond to the activation free-energy for cleavage of the tetramer core sequence AGCT (no flanking sequence), and actually corresponds to the predicted partial melting free-energy, $\Delta G_P$ (Table 1, eq 12) of the hypothetical four bp DNA with the sequence of the enzyme recognition site (e.g., 5'-AGCT-3').

The features along the enzyme/DNA reaction coordinate related to the duplex free-energy can be assessed by consideration of the simple classical scheme:

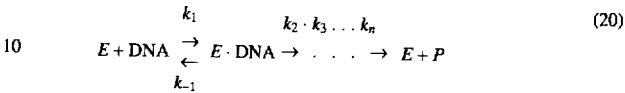

$$E+DNA \underset{k_{-1}}{\overset{k_1}{\rightleftarrows}} E\cdot DNA \xrightarrow{k_2\cdot k_3\ldots k_n} \ldots \rightarrow E+P \qquad (20)$$

E is the enzyme, E.DNA is the enzyme/DNA complex and P is the final cleaved product produced by E after a series of unknown intermediate steps with rate constants, $k_2, k_3, \ldots, k_n$. The product $k_2\cdot k_3 \ldots k_n = k_s$ represents all steps subsequent to binding. The composite rate constant for this reaction, $k_{comp}$, is given by:

$$k_{comp}=K_1 k_s[1+k_r/k_{-1}]^{-1} \qquad (21)$$

where $k_1$ and $k_{-1}$ are the forward and reverse rate constants for binding; $K_1=k_1/k_{-1}=\exp(-\Delta G_1/RT)$ is the equilibrium constant for binding; $k_s=A_{sc}\exp(-\Delta G^{++}s/RT)$ is the subsequent rate constant for product formation as defined hereinabove. The free-energy of binding is given by $\Delta G_1=-RT\ln K_1$ and the composite free-energy, $\Delta G^{++}=-RT\ln k_{comp}$. Thus eq 19 becomes:

$$\Delta G^{++}{=}\Delta G_1+\Delta G^{++}{}_s-RT\ln A_s-RT\ln(1+k_r/k_{-1}) \qquad (22)$$

Comparison of the cleavage rates with free-energies of melting is made by equating eqs 19 and 22:

$$\Delta G_1+\Delta G^{++}{}_s-RT\ln A_s-RT\ln(1+k_r/k_{-1})=\kappa(N)\Delta G_D+\Delta G^{++}(O) \qquad (23)$$

$\kappa(N)$ is a unitless function of sequence length but not sequence composition which relates the composite activation free-energy for reactivity to the free-energy of duplex melting. $\kappa(N)$ is determined from the slopes of the plots shown in FIG. 6.

Consideration of two DNAs of the same length with different sequences designated primed and unprimed allows direct determination of $\kappa(N)$ from the ratios of their rate constants, $k_{comp}$ and $k_{comp}'$, and melting free-energies, $\Delta G_D$ and $\Delta G_D'$, using eq 19:

$$\kappa(N)=RT\ln(k_{comp}'/k_{comp})/(\Delta G_D-\Delta G_D') \qquad (24)$$

The ratios of the rates are obtained from Table 5. From the data presented in Table 3 for the 12 and 20 bp molecules, $\kappa(12)=0.81$ and $\kappa(20)=0.26$. For the three 16 bp molecules the $(k_{comp}'/k_{comp})$ ratios and $(\Delta G_D-\Delta G_D')$ differences in eq 24 can be determined in three ways from any pair of values in the 16-mer set and yield, $\kappa K(N)=0.383\pm0.009$. In effect, $\kappa(N)$ is a measure of the fraction of duplex melting free-energy used in the composite activation energy of the cleavage reaction. For fragments of the same length, the rate of reaction with AluI restriction enzyme is directly proportional to stability of the duplex against melting. Results of studies of $(AT)_3$ and $(AA)_3$ hexadecamers with four different ligands are presented hereinafter. Results with these different ligands further corroborate the relationship between melting stability and reactivity.

Summary of Reactivity of Two 16 Base Pair DNAs With Four Ligands

Figure 7:
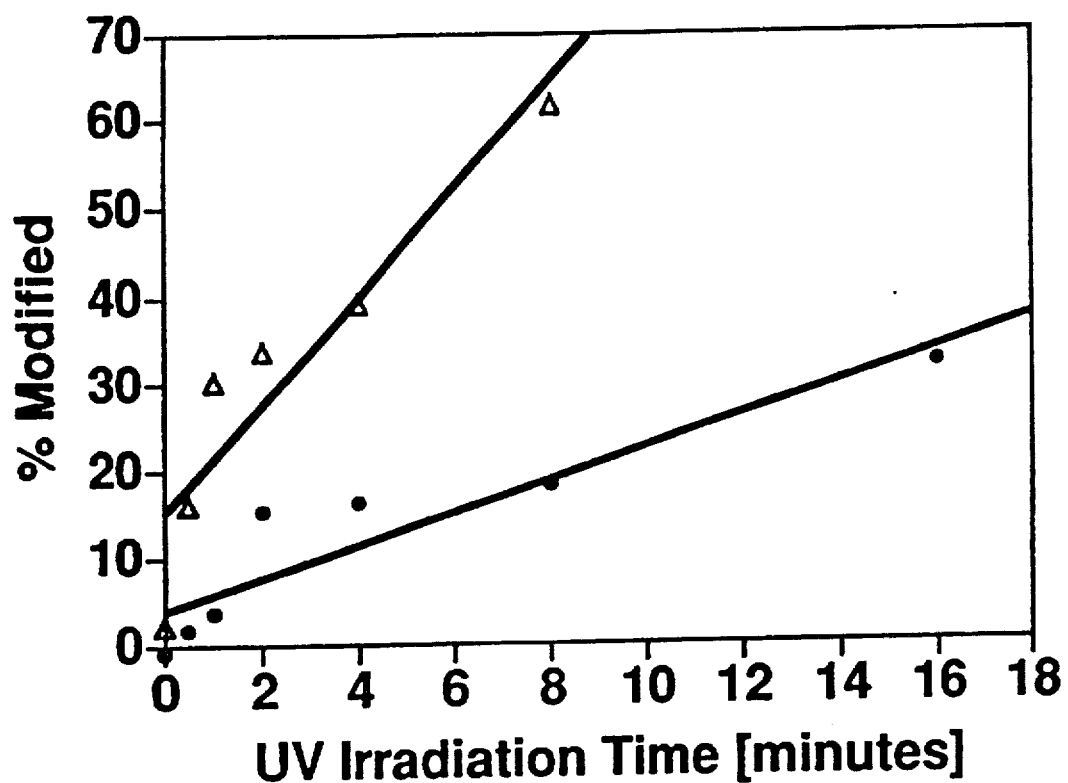
FIG. 7. Rate of Gilvocarcin V photoadduct formation with $(AT)_3AGCT(AT)_3$ (SEQ. ID NO: 2) duplex represented by open triangles and $(AA)_3AGCT(TT)_3$ (SEQ. ID NO: 3) duplex represented by closed circles. The percentage of each duplex modified is plotted as a function of time.

Results are provided hereinafter for the relative reactivity of four ligands: actinomycin D, gilvocarcin V, DNAseI and AluI with the $AT_3$ and $AA_3$ 16-mer duplexes. Actinomycin D and gilvocarcin V are minor groove intercalating compounds. DNaseI is a relatively ubiquitous minor groove cleaving endonuclease. AluI is a major groove site-specific endonuclease. Gilvocarcin V (toromycin, anandimycin, or GV) is an antibiotic isolated from *Streptomyces gilvotanareus* that has antitumor activity. H. Nakano, et al., *J. Antibiotics*, 34,271–75 (1981); K. Hatano, et al., *Agr. Biol. Chem.*, 44, 1157–63 (1980); D. M. Balitz, et al., *J. Antibiotics*, 3.4, 1544–55 (1981). Photoadduct formation of GV with oligonucleotides can be assayed by altered electrophoretic mobility of GV modified synthetic oligonucleotides. The relative rates of adduct formation (induced by uv light exposure) were determined for both hexadecamers under identical conditions (FIG. 7). The thermodynamically less stable duplex, $(AT)_3$, is at least 2.5 times more reactive than $(AA)_3$. The composite rates of reaction correspond qualitatively to differences in their relative stabilities. Observations of differential sequence-dependent reactivity of gilvocarcin with DNA are consistent with results of the AluI cleavage experiments. Further, both DNaseI and actinomycin D display the same behavior for these two sequences. In Table 6, results of studies of the four ligands with the two 16-mer duplexes are summarized.

What is claimed is:

1. A method for preparing at least one DNA sequence that can be employed as a flanking sequence to a DNA binding site for a ligand, wherein the DNA binding site is located within a preselected or native DNA sequence, to provide an increase in binding constant of the ligand for its DNA binding site, or an increase in composite rate of reaction of the ligand with the DNA binding site, relative to that for a preselected or native reference flanking sequence, which comprises:

iterating through the preselected or native DNA sequence to provide DNA subsequences;

selecting the DNA subsequences or permuting nucleotide bases of the DNA subsequences to provide potential DNA flanking sequences;

calculating free energies $\Delta G_D^o$ of duplex melting for each potential flanking sequence, which comprises:

summing free-energy values for hydrogen-bonding and stacking interactions for nucleotide bases constituting each potential flanking sequence, wherein such free-energy values are predetermined by semi-empirical thermochemical methods;

determining calculated composite reaction rates for the selected potential DNA flanking sequences by means of the equation:

$$\ln (k^{II}/k^{I}) = (\kappa/RT)(\Delta G_D^{oI} - \Delta G_D^{oII}),$$

or, if the composite reaction rates are binding limited, determining calculated binding constants by means of the equation:

$$\ln (K^{II}/K^{I}) = (\kappa/RT)(\Delta G_D^{oI} - \Delta G_D^{oII}),$$

wherein $k^{I}$ and $k^{II}$ are composite rate constants of a reaction for any two DNA sequences I and II, respectively, $K^{I}$ and $K^{II}$ are binding constants for the ligand to any two DNA sequences I and II, respectively, R is the universal gas constant, T is absolute temperature, $\kappa$ is a proportionality constant or function, wherein $\kappa$ is predetermined in accord with said equations for the ligand and for set sequence length by:
calculating free energies of melting $\Delta G_D^o$ for at least two preselected DNA flanking sequences if $\kappa$ is a proportionality constant, or at least three if a function, determined in accord with the summing step:
measuring composite rates of reaction or binding constants for synthetic or native DNA sequences containing the preselected DNA flanking sequences; and
relating the measured composite rates of reaction or binding constants to their respective differences in free-energy of melting $\Delta G_D^o$ as determined in accord with said equations; and choosing at least one potential DNA flanking sequence to serve as a DNA flanking sequence to a DNA binding site for a ligand providing an increase in binding constant of the ligand for its DNA binding site, or an increase in composite rate of reaction of the ligand with the DNA binding site, relative to that for a preselected or native reference flanking sequence; and preparing said DNA flanking sequence.

2. A method for preparing at least one DNA sequence that can be employed as a flanking sequence to a DNA binding site for a ligand, wherein the DNA binding site is located within a preselected or native DNA sequence, to provide a decrease in binding constant of the ligand for its DNA binding site, or a decrease in composite rate of reaction of the ligand with the DNA binding site, relative to that for a preselected or native reference flanking sequence, which comprises:

iterating through the preselected or native DNA sequence to provide DNA subsequences;

selecting the DNA subsequences or permuting nucleotide bases of the DNA subsequences to provide potential DNA flanking sequences;

calculating free energies $\Delta G_D^o$ of duplex melting for each potential flanking sequence, which comprises:
summing free-energy values for hydrogen-bonding and stacking interactions for nucleotide bases constituting each potential flanking sequence, wherein such free-energy values are predetermined by semi-empirical thermochemical methods;

determining calculated composite reaction rates for the selected potential D)NA flanking sequences by means of the equation:

$$\ln (k^{II}/k^{I}) = (\kappa/RT)(\Delta G_D^{oI} - \Delta G_D^{oII}),$$

or, if the composite reaction rates are binding limited, determining calculated binding constants by means of the equation:

$$\ln (K^{II}/K^{I}) = (\kappa/RT)(\Delta G_D^{oI} - \Delta G_D^{oII}),$$

wherein $k^{I}$ and $k^{II}$ are composite rate constants of a reaction for any two DNA sequences I and II binding constants for the ligand to any two DNA sequences I and II, respectively, R is the universal gas constant, T is absolute temperature, $\kappa$ is a proportionality constant or function, wherein $\kappa$ is predetermined in accord with said equations for the ligand and for set sequence length by:
calculating free energies of melting $\Delta G_D^o$ for at least two preselected DNA flanking sequences if $\kappa$ is a proportionality constant, or at least three if a function, determined in accord with the summing step;
measuring composite rates of reaction or binding constants for synthetic or native DNA sequences containing the preselected DNA flanking sequences; and
relating the measured composite rates of reaction or binding constants to their respective differences in free energy of melting $\Delta G_D^o$ as determined in accord with said equations; and choosing at least one potential DNA flanking sequence to serve as a DNA flanking sequence to a DNA binding site for a ligand providing a decrease in binding constant of the ligand for its DNA binding site, or a decrease in composite rate of reaction of the ligand with the DNA binding site, relative to that for a preselected or native reference flanking sequence; and preparing said DNA flanking sequence.

3. A method for preparing at least one DNA sequence that can be employed as a flanking sequence to a DNA binding site for a ligand, wherein the DNA binding site is located within a preselected or native DNA sequence, to provide an approximately equal binding constant of the ligand for its DNA binding site, or an approximately equal composite rate of reaction of the ligand with the DNA binding site, relative to that for a preselected or native reference flanking sequence, which comprises:

iterating through the preselected or native DNA sequence to select DNA subsequences;

selecting the DNA subsequences or permuting nucleotide bases of the DNA subsequences to provide potential DNA flanking sequences;

calculating free-energies $\Delta G_D^o$ of duplex melting for each potential DNA flanking sequence, which comprises:
summing free-energy values for hydrogen-bonding and stacking interactions for nucleotide bases constituting each potential DNA flanking sequence, wherein such free-energy values are predetermined by semi-empirical thermochemical methods;

determining calculated composite reaction rates for the potential DNA flanking sequences by means of the equation:

$$\ln (k^{II}/k^{I}) = (\kappa/RT)(\Delta G_D^{oI} - \Delta G_D^{oII}),$$

or, if the composite reaction rates are binding limited, determining calculated binding constants by means of the equation:

$$\ln (K^{II}/K^{I}) = (\kappa/RT)(\Delta G_D^{oI} - \Delta G_D^{oII}),$$

wherein $k^{I}$ and $k^{II}$ are composite rate constants of a reaction for any two DNA sequences I and II, respectively, $K^{I}$ and $K^{II}$ are binding constants for the ligand to any two DNA sequences I and II, respectively, R is the universal gas constant, T is absolute temperature, κ is a proportionality constant or function, wherein κ is predetermined in accord with said equations for the ligand and for set sequence length by:
calculating free energies of melting $\Delta G_D^o$ for at least two preselected DNA flanking sequences if κ is a proportionality constant, or at least three if a function, determined in accord with the summing step;
measuring composite rates of reaction or binding constants for synthetic or native DNA sequences containing the preselected DNA flanking sequences; and
relating the measured composite rates of reaction or binding constants to their respective differences in free energy of melting $\Delta G_D^o$ as determined in accord with said equations; and choosing at least one potential DNA flanking sequence to serve as a DNA flanking sequence to a DNA binding site for a ligand providing an approximately equal binding constant of the ligand for its DNA binding site, or an approximately equal composite rate of reaction of the ligand with the DNA binding site, relative to that for a preselected or native reference flanking sequence; and preparing said DNA flanking sequence.

4. The method according to claim 3, wherein at least one set of DNA primers is prepared which amplify or generate amplification products for at least two different regions from a corresponding preselected or native DNA sequence at approximately equal rates, which comprises:

iterating through the preselected or native DNA sequence to select at least one DNA subsequence for use as a potential DNA primer or set of DNA primers;

calculating free energies $\Delta G_D^o$ of duplex melting for each potential DNA primer, which comprises:
summing free-energy values for hydrogen-bonding and stacking interactions for nucleotide bases constituting each potential DNA primer, wherein such free-energy values are predetermined by semi-empirical thermochemical methods;

determining calculated composite reaction rates for amplifying the corresponding preselected or native DNA sequence using each selected or permuted potential DNA primer or set of DNA primers by means of the equation:

$$\ln (k''/k') = (\kappa/RT)(\Delta G_D^{oI} - \Delta G_D^{oII}),$$

or, if the composite reaction rates are binding limited, determining calculated binding constants of the corresponding preselected DNA sequence by means of the equation:

$$\ln (k''/k') = (\kappa/RT)(\Delta G_D^{oI} - \Delta G_D^{oII}),$$

wherein $k'$ and $k''$ are composite reaction rate constants for amplification using potential DNA primers I and II, respectively, $K''$ and $K''$ are binding constants for an amplifying reagent binding to the preselected or native DNA sequence to which potential DNA primers I and II anneal, respectively, R is the universal gas constant, T is absolute temperature, κ is a proportionality constant or function.

wherein k is predetermined in accord with said equations for the amplifying f amplification or binding with potential DNA primers or set of potential DNA primers I and II to their respective differences in free energies of melting $\Delta G_D^{oI}$ and $\Delta G_D^{oII}$, which comprises:
calculating free energies of melting $\Delta G_D^o$ for at least two potential DNA primers if κ is a proportionality constant, or at least three if a function, determined in accord with the summing step;
measuring composite rates of amplification or generation of amplification products or binding constants for synthetic or native DNA sequences to which the potential DNA primers anneal; and
relating the measured composite rates of reaction or binding constants to their respective differences in free energy of melting $\Delta G_D^o$ in accord with said equations; and
synthesizing the potential DNA primers by chemical or biochemical methods;
measuring composite reaction rates of amplification or generation of amplification products using the potential DNA primers by any method suited for the purpose;
repeating the iterating, calculating, synthesizing and measuring steps to determine at least one additional potential DNA primer which amplifies the preselected or native DNA sequence, does not interact with any other primer, and has a composite reaction rate approximately equal to that of the first potential DNA primer or set of potential DNA primers; and
choosing at least one set of potential DNA primers with approximately equal calculated composite reaction rates for amplifying or generating amplification products for at least two different regions from the corresponding preselected or native DNA sequence using each set of potential DNA primers, wherein calculated composite reaction rates fall within a predefined deviation about a mean composite reaction rate.

5. A method of detecting the presence or absence of a preselected or native DNA sequence or sequences which comprises determining at least one set of DNA primers which amplify, or generate amplification products for, at least two different regions from the preselected or native DNA sequence at approximately equal rates, by:

iterating through the preselected or native DNA sequence to select at least one DNA subsequence for use as a potential DNA primer or set of DNA primers;

calculating free energies $\Delta G_D^o$ of duplex melting for each potential DNA primer, which comprises:
summing free-energy values for hydrogen-bonding and stacking interactions for nucleotide bases constituting each potential DNA primer, wherein such free-energy values are predetermined by semi-empirical thermochemical methods;

determining calculated composite reaction rates for amplifying the corresponding preselected or native DNA sequence using each selected or permuted potential DNA primer or set of DNA primers by means of the equation:

$$\ln (k''/k') = (\kappa/RT)(\Delta G_D^{oI} - \Delta G_D^{oII}),$$

or, if the composite reaction rates are binding limited, determining calculated binding constants of the corresponding preselected DNA sequence by means of the equation:

$$\ln (k''/k') = (\kappa/RT)(\Delta G_D^{oI} - \Delta G_D^{oII}),$$

wherein $k'$ and $k''$ are composite reaction rate constants for amplification using potential DNA primers I and II, respectively, $K'$ and $K''$ are binding constants for an amplifying reagent binding to the preselected or native DNA sequence to which potential DNA primers I and II anneal, respectively, R is the universal gas constant, T is absolute temperature, $\kappa$ is a proportionality constant or function.

wherein $\kappa$ is predetermined in accord with said equations for the amplifying reagent and for set sequence length by relating measured composite rates of amplification or binding with potential DNA primers or set of potential DNA primers I and II to their respective differences in free energies of melting $\Delta G_D^{oI}$ and $\Delta G_D^{oII}$, which comprises:

calculating free energies of melting $\Delta G_D^o$ for at least two potential DNA primers if $\kappa$ is a proportionality constant, or at least three if a function, determined in accord with the summing step;

measuring composite rates of amplification or generation of amplification products or binding constants for synthetic or native DNA sequences to which the potential DNA primers anneal; and relating the measured composite rates of reaction or binding constants to their respective differences in free energy of melting $\Delta G_D^o$ in accord with said equations; and synthesizing the potential DNA primers by chemical or biochemical methods;

measuring composite reaction rates of amplification or generation of amplification products using the potential DNA primers by any method suited for the purpose;

repeating the iterating, calculating, synthesizing and measuring steps to determine at least one additional potential DNA primer which amplifies, or generates amplification products for, the preselected or native DNA sequence, does not interact with any other primer, and has a composite reaction rate approximately equal to that of the first potential DNA primer or set of potential DNA primers; and choosing at least one set of potential DNA primers with approximately equal calculated composite reaction rates for amplifying, or generating amplification products for, at least two different regions from the corresponding preselected or native DNA sequence using each set of potential DNA primers, wherein calculated composite reaction rates fall within a predefined deviation about a mean composite reaction rate; and using at least one set of potential DNA primers to detect the presence or absence of a preselected or native DNA sequence, which comprises:

combining aliquots of at least one set of DNA primers with an analytical unknown sample which may or may not contain a preselected or native DNA sequence;

performing the amplifying reaction to generate amplified concentrations or amplification products of the preselected or native DNA sequence, if present; and observing by any suitable qualitative or quantitative method the presence or absence of, the preselected or native DNA sequence, thereby detecting the presence or absence of the preselected or native DNA sequence.

6. The method in accord with claim 5 of detecting the presence or absence of a preselected or native DNA sequence or sequences, wherein the presence or absence of a preselected or native DNA sequence or sequences in a subject indicates that the subject is suffering from a disease or diseases related to the respective preselected or native DNA sequence or sequences, which comprises determining at least one set of DNA primers which amplify, or generate amplification products for, at least two different regions from the corresponding DNA sequence at approximately equal rates, which comprises:

iterating through the preselected or native DNA sequence or sequences to select at least one DNA subsequence for use as a potential DNA primer or set of DNA primers;

calculating free energies $\Delta G_D^o$ of duplex melting for each potential DNA primer, which comprises:

summing free-energy values for hydrogen-bonding and stacking interactions for nucleotide bases constituting each potential DNA primer, wherein such free-energy values are predetermined by semi-empirical thermochemical methods;

determining calculated composite reaction rates for amplifying, or generating amplification products for, the corresponding preselected or native DNA sequence or sequences using each potential selected or permuted DNA primer or set of DNA primers by means of the equation:

$$\ln (k''/k') = (\kappa/RT)(\Delta G_D^{oI} - \Delta G_D^{oII}),$$

or, if the composite reaction rates are binding limited, determining calculated binding constants of the corresponding preselected or native DNA sequences by means of the equation:

$$\ln (k''/k') = (\kappa/RT)(\Delta G_D^{oI} - \Delta G_D^{oII}),$$

wherein $k'$ and $k''$ are composite reaction rate constants for amplification using potential DNA primers I and II, respectively, $K'$ and $K''$ are binding constants for an amplifying reagent binding to the preselected or native DNA sequence to which potential DNA primers I and II anneal, respectively, R is the universal gas constant, T is absolute temperature, $\kappa$ is a proportionality constant or function, wherein $\kappa$ is predetermined in accord with said equations for the amplifying reagent and for set sequence length by relating measured composite rates of amplification or binding with potential DNA primers or set of potential DNA primers I and II to their respective differences in free energies of melting $\Delta G_D^{oI}$ and $\Delta G_D^{oII}$, which comprises:

calculating free energies of melting $\Delta G_D^o$ or at least two potential D)NA primers if $\kappa$ is a proportionality constant, or at least three if a function, determined in accord with the summing step:

measuring composite rates of amplification or generation of amplification products or binding constants for synthetic or native DNA sequences to which the potential DNA primers anneal; and relating the measured composite rates of reaction or binding constants to their respective differences in free energy of melting $\Delta G_D^o$ in accord with said equations; and synthesizing the potential DNA primers by chemical or biochemical methods;

measuring composite reaction rates of amplification or generation of amplification products using the potential DNA primers by any method suited for the purpose;

repeating the iterating, calculating, synthesizing and measuring steps to determine at least one additional potential DNA primer which amplifies, or generates amplification products for, the preselected or native DNA sequence, does not interact with any other primer, and has a composite reaction rate approximately equal to that of the first potential DNA primer or set of potential DNA primers; and choosing at least one set of potential DNA primers with approximately equal calculated composite reaction rates for amplifying, or generating amplification products for, at least two different regions from the corresponding preselected or native DNA sequence using each set of potential DNA primers, wherein the calculated composite reaction rates fall within a predefined deviation about a mean composite reaction rate; and using at least one set of potential DNA primers for two different regions of the preselected or native DNA sequence or sequences to detect the presence or absence of a preselected or native DNA sequence or sequences, which if present indicates that a subject is suffering from a disease or diseases related to the respective preselected or native DNA sequence or sequences, which comprises:

combining aliquots of at least one set of DNA primers with an analytical unknown sample which may or may not contain a preselected or native DNA sequence or sequences;

performing the amplification reaction to generate amplified concentrations or amplification products of the preselected or native DNA sequence or sequences, if present; and observing by any suitable qualitative or quantitative method the presence or absence of, the preselected or native DNA sequence or sequences, thereby detecting the presence or absence of the preselected or native DNA sequence or sequences, which if present indicates that a subject is suffering from a disease or diseases related to the respective preselected or native DNA sequence or sequences.

7. The method in accord with claim 5 of detecting the presence or absence of a DNA sequence or sequences, wherein said DNA sequence or sequences correspond to human immunodeficiency virus, which comprises determining at least one set of DNA primers which amplify, or generate amplification products for, at least two different regions from the corresponding DNA sequence at approximately equal rates, which comprises:

iterating through the DNA sequence or sequences corresponding to human immunodeficiency virus to select at least one DNA subsequence for use as a potential DNA primer or set of DNA primers;

calculating free energies $\Delta G_D^o$ of duplex melting for each potential DNA primer, which comprises:
summing free-energy values for hydrogen-bonding and stacking interactions for nucleotide bases constituting each potential DNA primer, wherein such free-energy values are predetermined by semi-empirical thermochemical methods;

determining calculated composite reaction rates for amplifying, or generating amplification products for, the corresponding D)NA sequence or sequences using each selected or permuted potential DNA primer or set of DNA primers by means of the equation:

$$\ln (k^{II}/k^{I}) = (\kappa/RT)(\Delta G_D^{oI} - \Delta G_D^{oII}),$$

or, if the composite reaction rates are binding limited, determining calculated binding constants of the corresponding preselected or native DNA sequences by means of the equation:

$$\ln (k^{II}/k^{I}) = (\kappa/RT)(\Delta G_D^{oI} - \Delta G_D^{oII}),$$

wherein $k^I$ and $k^{II}$ are composite reaction rate constants for amplification using potential DNA primers I and II, respectively, $K^I$ and $K^{II}$ are binding constants for an amplifying reagent binding to the DNA sequence to which potential DNA primers I and II anneal, respectively, R is the universal gas constant, T is absolute temperature, $\kappa$ is a proportionality constant or function, wherein $\kappa$ is predetermined in accord with said equations for the amplifying reagent and for set sequence length by relating measured composite rates of amplification or binding with potential DNA primers or set of potential DNA primers I and II their respective differences in free energies of melting $\Delta G_D^{oI}$ and $\Delta G_D^{oII}$, which comprises:

calculating free energies of melting $\Delta G_D^o$ for at least two potential DNA primers if $\kappa$ is a proportionality constant, or at least three if a function, determined in accord with the summing step:

measuring composite rates of amplification or generation of amplification products or binding constants for synthetic or native DNA sequences to which the potential DNA primers anneal; and relating the measured composite rates of reaction or binding constants to their respective differences in free energy of melting $\Delta G_D^o$ in accord with said equations: and synthesizing the potential DNA primers by chemical or biochemical methods;

measuring composite reaction rates of amplification or generation amplification products using the potential DNA primers by any method suited for the purpose;

repeating the iterating, calculating, synthesizing and measuring steps to determine at least one additional potential DNA primer which amplifies, or generates amplification products for, the DNA sequence, does not interact with any other primer, and has a composite reaction rate approximately equal to that of the first potential DNA primer or set of potential DNA primers; and choosing at least one set of potential DNA primers with approximately equal calculated composite reaction rams for amplifying, or generating amplification products for, at least two different regions from the corresponding DNA sequence using each set of potential DNA primers, wherein the calculated composite reaction rates fall within a predefined deviation about a mean composite reaction rate; and using at least one set of potential DNA primers for two different regions of the DNA sequence or sequences to detect the presence or absence of the DNA sequence or sequences corresponding to human immunodeficiency virus, which comprises:

combining aliquots of at least two potential DNA primers with an analytical sample which may or may not contain the DNA sequence or sequences;

performing the amplification reaction to generate amplified concentrations or amplification products of the DNA sequence or sequences, if present; and observing by any suitable qualitative or quantitative method the presence or absence of, the DNA sequence or sequences corresponding to human immunodeficiency virus, thereby detecting the presence or absence of the DNA sequence or sequences corresponding to human immunodeficiency virus.

8. The method of claim 4, wherein the method for measuring composite reaction rates of amplification or generation of amplification products using the potential DNA primers is selected from the group consisting of gel techniques, spectroscopic methods, electrochemical methods, and biochemical assay methods.

9. The method of claim 5, wherein the method for measuring composite reaction rates of amplification or generation of amplification products using the potential DNA primers is selected from the group consisting of gel techniques, spectroscopic methods, electrochemical methods, and biochemical assay methods, and wherein the suitable qualitative or quantitative method for observing the presence or absence of the preselected or native DNA sequence or sequences is selected from the group consisting of gel techniques, spectroscopic methods, electrochemical methods, and biochemical assay methods.

10. The method of claim 6, wherein the method for measuring composite reaction rates of amplification or generation of amplification products using the potential DNA primers is selected from the group consisting of gel techniques, spectroscopic methods, electrochemical methods, and biochemical assay methods, and wherein the suitable qualitative or quantitative method for observing the presence or absence of the preselected or native DNA sequence or sequences is selected from the group consisting of gel techniques, spectroscopic methods, electrochemical methods, and biochemical assay methods.

11. The method of claim 7, wherein the method for measuring composite reaction rates of amplification or generation of amplification products using the potential DNA primers is selected from the group consisting of gel techniques, spectroscopic methods, electrochemical methods, and biochemical assay methods, and wherein the suitable qualitative or quantitative method for observing the presence or absence of the DNA sequence or sequences corresponding to human immunodeficiency virus is selected from the group consisting of gel techniques, spectroscopic methods, electrochemical methods, and biochemical assay methods.

* * * * *

UNITED STATES PATENT AND TRADEMARK OFFICE
CERTIFICATE OF CORRECTION

PATENT NO. : 5,593,834
DATED : January 14, 1997
INVENTOR(S) : Michael J. Lane et al.

It is certified that error appears in the above-identified patent and that said Letters Patent is hereby corrected as shown below:

At column 29, line 59, please replace "D)NA" with --DNA--;

At column 31, line 58, please replace "$K^{II}$ and $K^{II}$" with --$K^I$ and $K^{II}$--;

At column 31, line 65, please replace "amplifying f amplification" with --amplifying reagent and for set sequence length by relating measured composite rates of amplification--; and At column 35, line 65, please replace "D)NA" with --DNA--.

Signed and Sealed this

Tenth Day of November 1998

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

AAATATAGCT ATATTTAAAT ATAGCTATAT TT    32

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

ATATATAGCT ATATAT    16

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

AAAAAAAGCT TTTTTT    16

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
ATATAGCTAT  AT                                                                        1 2
```

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
AAAAGCTTT  TT                                                                         1 2
```

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

```
AAATATAGCT  ATATTT                                                                    1 6
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

```
ATATATATAG  CTATATATAT                                                                2 0
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

```
AAAAAAAAAG  CTTTTTTTTT                                                                2 0
```